(12) United States Patent
Somers et al.

(10) Patent No.: US 9,683,031 B2
(45) Date of Patent: Jun. 20, 2017

(54) BIOMARKERS FOR RHEUMATOID ARTHRITIS

(75) Inventors: Veerle Somers, Sint-Truiden (BE);
Klaartje Somers, Vliermaalroot (BE);
Pieter Stinissen, Diepenbeek (BE)

(73) Assignee: UNIVERSITEIT HASSELT, Diepenbeek (BE)

( * ) Notice: Subject to any disclaimer, the term of this patent is extended or adjusted under 35 U.S.C. 154(b) by 1041 days.

(21) Appl. No.: 12/737,281

(22) PCT Filed: Mar. 23, 2009

(86) PCT No.: PCT/EP2009/053369
§ 371 (c)(1),
(2), (4) Date: May 11, 2011

(87) PCT Pub. No.: WO2009/115612
PCT Pub. Date: Sep. 24, 2009

(65) Prior Publication Data
US 2011/0212470 A1    Sep. 1, 2011

Related U.S. Application Data

(60) Provisional application No. 61/038,481, filed on Mar. 21, 2008.

(51) Int. Cl.
*G01N 33/566* (2006.01)
*C07K 14/47* (2006.01)
*C07K 16/18* (2006.01)
*G01N 33/68* (2006.01)

(52) U.S. Cl.
CPC ......... *C07K 16/18* (2013.01); *G01N 33/6854* (2013.01); *G01N 2800/102* (2013.01)

(58) Field of Classification Search
CPC .......................... C07K 16/18; G01N 2800/102
See application file for complete search history.

(56) References Cited

U.S. PATENT DOCUMENTS

| 5,585,464 A | 12/1996 | Prakash |
| 5,888,833 A | 3/1999 | Serre et al. |
| 6,858,438 B2 | 2/2005 | Van Venrooij et al. |
| 2007/0264673 A1 | 11/2007 | Wild et al. |
| 2010/0111993 A1* | 5/2010 | Tureci et al. ............. 424/192.1 |

FOREIGN PATENT DOCUMENTS

| WO | WO 01/46222 | 6/2001 |
| WO | WO 01/57182 A | 8/2001 |
| WO | WO 2005038030 A1 * | 4/2005 |

(Continued)

OTHER PUBLICATIONS

Trouw et al., Autoimmunity Reviews 12:318-322 (Jun. 1, 2012).*

(Continued)

*Primary Examiner* — Randall L Beane
(74) *Attorney, Agent, or Firm* — Jones Day

(57) ABSTRACT

The present invention relates to the diagnosis of autoimmune disorders, more specifically to the diagnosis of rheumatoid disorders, chronic autoimmune arthritis and even more specifically to the diagnosis of rheumatoid arthritis. A biomarker panel is provided which can be used to detect if a subject has rheumatoid arthritis. Also described are methods of identification of such biomarkers.

12 Claims, 12 Drawing Sheets

(56) References Cited

FOREIGN PATENT DOCUMENTS

Figure 1:
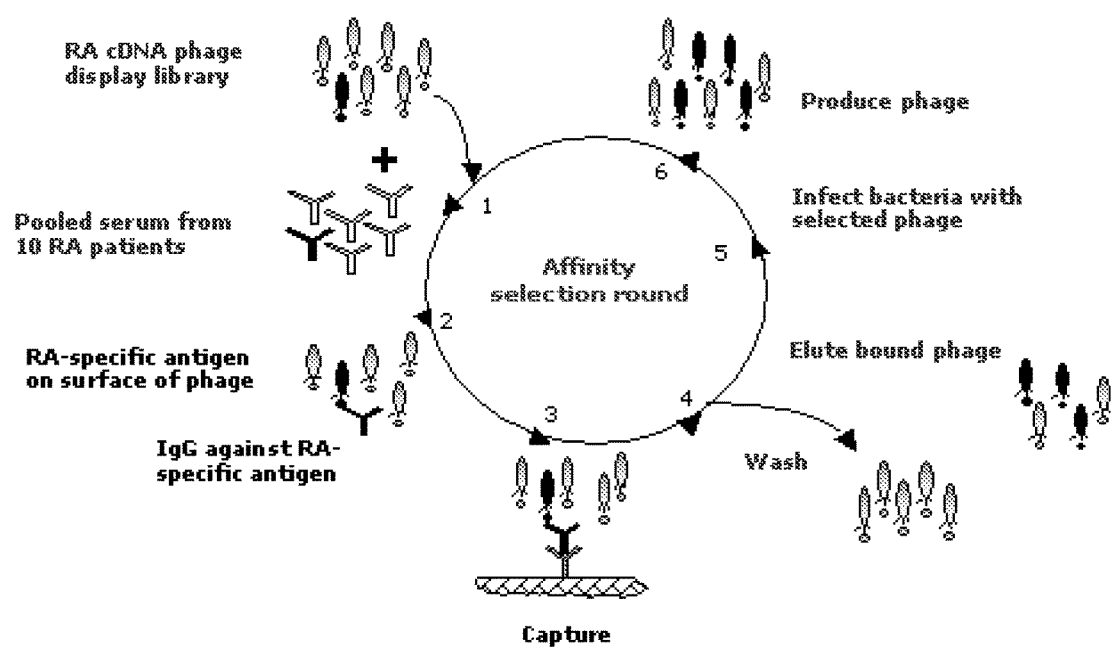

| WO | WO 2005/064307 | 7/2005 |
|---|---|---|
| WO | WO 2007/017556 | 2/2007 |
| WO | WO 2009/115612 A1 | 9/2009 |

OTHER PUBLICATIONS

"Autoantigen", Merrian-Webster.com, attached as pdf, also available at http://www.merriam-webster.com/medical/autoantigen (last visited Dec. 3, 2014).*
Mayeux, Biomarkers: Potential Uses and Limitations, J. of the Am. Soc. for Exp. NeuroTherapeutics, vol. 1:182-188 (2004).*
"Autoantibody", TheFreeDictionary, attached as pdf, available at http://medical-dictionary.thefreedictionary.com/Autoantibodies (last visited Dec. 18, 2014).*
Gerber, The Journal of Clinical Investigation, vol. 55:1164-1173 (Jun. 1975).*
Rheumatology Nurse Newsletter, vol. 6(4): 1-16 (Dec. 15, 2013).*
"Autoantibody", www.Dictionary.com, 3 pages (2016), also available at http://www.dictionary.com/browse/autoantibody (last visited Jun. 13, 2016); at p. 1).*
NCBI, WP_029456696, two-component sensor histidine kinase [Desulfovibrio alcoholivorans], 2 pages (Nov. 20, 2015), also available at http://www.ncbi.nlm.nih.gov/protein/WP_029456696 (last visited Jun. 13, 2016).*
Chatterjee et al., Role of 5' and 3' untranslated regions of mRNAs in human Diseases, Biol. Cell (2009), vol. 101:251-262 (May 2009).*
Mouilleron et al., Survey and Summary: Death of a dogma: eukaryotic mRNAs can code for more than one protein, Nucleic Acids Research vol. 44(1):14-23 (Nov. 17, 2015).*
Gertz et. al., BMC Biology, vol. 4:41, 14 pages (Dec. 7, 2006).*
"Biomarker", NIH Cancer Institute, NCI Dictionary of Cancer Terms, www.cancer.gov, attached as pdf, 1 page, also available at http://www.cancer.gov/publications/dictionaries/cancer-terms?cdrid=45618 (last visited Jun. 15, 2016).*
Mahler et al. (J. Mol. Med., vol. 79:722-731 (2001).*
BEST(Biomarkers, EndpointS, and other Tools) Resource [Internet], last updated Apr. 28, 2016, ncbi.nlm.nig.gov, 13 pages, also available at http://www.ncbi.nlm.nih.gov/books/NBK338448/#IX-B (last visited Jun. 15, 2016).*
"Autoantigen", Wiktionary.org, 1 page, also available at https://en.wiktionary.org/wiki/autoantigen (last visited Jun. 16, 2016).*
Vohr, Encyclopedic Reference of Immunotoxicology, ISBN 9783540278061, DOI 10.1007/3-540-27806-0, Reference Chapter for "A", 82 pages (2005 ed.).*
"Autoantigen", www.medilexicon.com, 2 pages, also available at http://www.medilexicon.com/medicaldictionary.php?t=8694 (last visited Jun. 16, 2016).*
Baert, Encyclopedia of Diagnostic Imaging, ISBN: 978-3-540-35278-5 (Print) 978-3-540-35280-8 (Online), Reference works "B", 99 pages (2008).*
Offermanns et al., Encyclopedia of Molecular Pharmacology, ISBN: 978-3-540-38916-3 (Print) 978-3-540-38918-7 (Online), Reference works "B", pp. 245-289 (2008).*
Redei, Encyclopedia of Genetics, Genomics, Proteomics and Informatics, ISBN: 978-1-4020-6753-2 (Print) 978-1-4020-6754-9 (Online), Reference works "B", pp. 177-245 (2008).*
Winter et al. (AB0262 Seroconversion and Fluctuation of Current and Novel Biomarkers during disease Course of RA, EULAR 2014: Scientific abstracts, Ann Rehem Dis., vol. 73:891 (2014) (abstract only).*
Lee et al., Clinical utility of the anti-CCP assay in patients with rheumatic diseases, International Journal of Gynaecology & Obstetrics, Sep. 1, 2003, pp. 870-874, vol. 62, No. 9, Limerick, IR.
PCT International Search Report, PCT/EP2009/053369 dated Aug. 11, 2009.
Somers et al., "Novel autoantibody markers for early seronegative rheumatoid arthritis," J. Autoimmun. 36(1):33-46 (2011) (Epub Nov. 10, 2010).

\* cited by examiner a b

BIOMARKERS FOR RHEUMATOID ARTHRITIS

PRIORITY CLAIM

This is a national phase entry under 35 U.S.C. §371 of International Patent Application PCT/EP2009/053369, filed Mar. 23, 2009, published in English as International Patent Publication WO 2009/115612 A1 on Sep. 24, 2009, which claims the benefit under Article 8 of the Patent Cooperation Treaty to U.S. Provisional Patent Application Ser. No. 61/038,481, filed Mar. 21, 2008.

FIELD OF THE INVENTION

The present invention relates to the diagnosis of autoimmune disorders, more specifically to the diagnosis of rheumatoid disorders, chronic autoimmune arthritis and even more specifically to the diagnosis of rheumatoid arthritis. A biomarker panel is provided which can be used to detect if a subject has rheumatoid arthritis. Also described are methods of identification of such biomarkers.

BACKGROUND TO THE INVENTION

Rheumatoid Arthritis (RA) is the most frequent form of chronic autoimmune arthritis, affecting 0.5-1% of the adult world population (1). The disease is characterised by joint pain, swelling and stiffness, due to synovitis and irreversible joint destruction, ultimately leading to functional disability. At present, RA is diagnosed based on fulfilment of the classification criteria set by the American College of Rheumatology (ACR) in 1987. If at least 4 out of 7 of these primarily clinical classification criteria are fulfilled, the patient is diagnosed with RA (2). The presence of rheumatoid factor (RF) is the only criterion for diagnosis based on objective laboratory findings. The performance of these classification criteria is however far from optimal, especially for early RA. The disease course of early RA is very heterogeneous and early RA patients often do not fulfil 4 of the 7 criteria (3). Also, to meet the ACR criteria, symptoms must last for 6 weeks or more. This results in a low diagnostic sensitivity for RA, ranging from 62% to 90%, and a pronounced diagnostic delay (3-6). Early treatment of RA is however essential in preventing irreversible joint destruction and improving disease outcome, so that early diagnosis of the disease is of utmost importance (7-9).

To improve diagnostic efficiency, it is currently recommended to incorporate anti-CCP antibody (anti-cyclic-citrullinated-peptides antibody, ACPA) testing in addition to RF testing in the diagnostic work-up, as to maximize sensitivity by combining the two markers (3;10;11). In addition to being an early and specific RA marker, anti-CCP antibodies are predictive for RA development in undifferentiated arthritis patients, and presence of these markers in RA is associated with a worse disease course (11-15). However, according to recently published meta-analyses of studies regarding ACPA and RF testing in RA, the sensitivity of anti-CCP antibodies is only moderate (67-68%) despite a high specificity of 95% (16;17). This would imply that 33% of RA patients is anti-CCP antibody negative (ACPA−). The reported sensitivity for ACPA testing in early disease is even lower (16). Moreover, recent findings indicate a potentially different aetiology and pathogenesis in ACPA negative and ACPA positive RA (18-20). This heterogeneity implies the need for a panel of different markers to achieve an accurate diagnosis for the entire RA patient population.

SUMMARY

Therefore, the identification of additional RA disease markers is crucial, particularly for early RA and RF negative (RF−) ACPA negative (ACPA−) RA. In the present invention we analysed autoantibody profiles in early and RF− ACPA− RA patients with a high-throughput molecular technique called Serological Antigen Selection (SAS) to identify additional RA (auto)antigen targets and corresponding autoantibodies that can be used as serological markers. The SAS procedure is based on phage display of a cDNA expression library, made from RA synovial tissue, which is screened with pooled serum from RA patients. By performing several rounds of affinity selection of the RA cDNA phage display library with pooled immunoglobulines (IgG) from RA patients, enrichment of RA-associated target cDNA clones occurred. The present invention provides a set of biomarkers which are highly specific for RA patients, particularly RA patients with a disease duration of less than one year and serum which is RF negative and/or ACPA-negative.

Accordingly, in a first aspect, methods are provided for specifically detecting rheumatoid arthritis in a mammal comprising i) detecting the presence or quantity of at least one antibody in a body fluid derived from said mammal wherein said antibody has a specificity for a polypeptide comprising a sequence selected from the group consisting of SEQ ID NO: 1-14 or a fragment comprising at least 5 consecutive amino acids derived from SEQ ID NO: 1-14 and wherein ii) the presence of said antibody indicates that said mammal suffers from rheumatoid arthritis.

In particular embodiments, the mammal to be diagnosed is a human.

According to particular embodiments, the body fluid derived from the mammal is blood plasma, blood serum or synovial fluid.

According to specific embodiments, detection is via immune-enzymatic processes such as, but not limited to, enzyme-linked immunosorbant assays (ELISA), immunofluorescent techniques, radioimmunological assays (RIA) and immunoblotting and LINE blot. According to alternative embodiments, detection is via flow cytometry.

The detection and/or quantification of at least one specific antibody according to the methods described herein may be indicative for rheumatoid arthritis. According to particular embodiments, the detection and/or quantification of at least one specific antibody is indicative for rheumatoid arthritis with a disease stage of less than 1 year. According to alternative specific embodiments, the detection and/or quantification of at least one specific antibody is indicative for rheumatoid arthritis in a patient which body fluid is seronegative for rheumatoid factor and/or anti-CCP antibodies.

According to particular embodiments, the methods described herein further comprise the detection of rheumatoid factor. According to alternative particular embodiments, the methods involve the detection of antibodies against cyclic citrullinated peptides. Notably, the methods may comprise the detection of rheumatoid factor as well as of antibodies against cyclic citrullinated peptides.

According to a second aspect of the invention, polypeptides (i.e. at least one polypeptide) are provided that can be used as biomarkers or to assist in diagnosis, e.g. of rheumatoid arthritis. Such polypeptide consists essentially of a sequence selected from SEQ ID NO: 1-14 or a fragment thereof comprising at least 5 consecutive amino acids derived from SEQ ID NO: 1-14. With 'consisting essentially of' it is meant that other amino acids may be included, i.e. the sequence may be part of a larger polypeptide; however, it should be noted that this term also implies that the defined sequence is the most important part of the molecule. Thus, a polypeptide consisting essentially of a defined sequence (SEQ ID NO: 1-14) is necessarily less than double the length of the defined sequence. According to a most specific embodiment, the polypeptide consists of a sequence selected from SEQ ID NO: 1-14 or a fragment thereof comprising at least 5 consecutive amino acids derived from SEQ ID NO: 1-14.

In another particular embodiment, compositions are provided comprising at least one polypeptide comprising a sequence selected from SEQ ID NO: 1-14 or a fragment thereof comprising at least 5 consecutive amino acids derived from SEQ ID NO: 1-14. In a further specific embodiment, the composition consists essentially of at least one polypeptide.

According to another particular embodiment, compositions are provided comprising at least two different polypeptides comprising a sequence represented by any of SEQ ID NO: 1-14 or a fragment comprising at least 5 consecutive amino acids derived from SEQ ID NO: 1-14. Here also, it is envisaged that in specific embodiments the compositions consist essentially of the at least two different polypeptides.

As mentioned, the polypeptides can be used as biomarkers or to assist in diagnosis, e.g. of rheumatoid arthritis. Accordingly, in a further aspect, the polypeptides and compositions described herein are envisaged for use as a diagnostic.

According to yet a further aspect, the (in vitro) use of the polypeptides or compositions described herein for detecting the presence and/or quantity of specific antibodies to the polypeptide or to at least one polypeptide of said composition in a body fluid of a mammal is provided.

According to specific embodiments, the mammal of which the body fluid is tested is a human. According to other specific embodiments, the body fluid is blood plasma, blood serum or synovial fluid.

According to particular embodiments, detection occurs via immune-enzymatic processes comprising enzyme-linked immunosorbant assays (ELISA), immunofluorescent techniques, radioimmunological assays (RIA), immunoblotting and LINE blot. According to alternative particular embodiments, flow cytometry is used for detection.

According to particularly envisaged embodiments, the detection and/or quantification of at least one specific antibody is indicative for rheumatoid arthritis. According to particular embodiments, the detection and/or quantification of at least one specific antibody is indicative for rheumatoid arthritis with a disease stage of less than 1 year. According to alternative specific embodiments, the detection and/or quantification of at least one specific antibody is indicative for rheumatoid arthritis in a patient which body fluid is seronegative for rheumatoid factor and/or anti-CCP antibodies.

According to particular embodiments, the uses described herein further comprise the detection of rheumatoid factor. According to alternative particular embodiments, the uses involve the detection of antibodies against cyclic citrullinated peptides. Notably, the uses may comprise the detection of rheumatoid factor as well as of antibodies against cyclic citrullinated peptides.

In a further aspect, methods are provided for evaluating the prognosis and/or disease severity of rheumatoid arthritis in a patient comprising i) detecting the decrease or increase of at least one antibody in a body fluid derived from said patient wherein said antibody has a specificity for a polypeptide comprising a sequence selected from the group consisting of SEQ ID NO: 1-14 or a fragment comprising at least 5 consecutive amino acids derived from SEQ ID NO: 1-14 and wherein ii) the presence or decreased/increased concentration of said antibody indicates the prognosis of rheumatoid arthritis in said patient.

According to another aspect, methods are envisaged for selecting a patient for a specific therapeutic treatment of rheumatoid arthritis or evaluating the therapeutic treatment of rheumatoid arthritis in a patient comprising i) detecting the presence or quantity of at least one antibody in a body fluid derived from said patient wherein said antibody has a specificity for a polypeptide comprising a sequence selected from the group consisting of SEQ ID NO: 1-14 or a fragment comprising at least 5 consecutive amino acids derived from SEQ ID NO: 1-14 and wherein ii) the decreased or increased concentration of said antibody leads to an election of a specific therapeutic treatment of rheumatoid arthritis in said patient.

According to a further aspect, diagnostic kits are provided for the detection of rheumatoid arthritis comprising at least one polypeptide as described herein, or a composition as described herein, as well as reagents for making a medium appropriate for an immunological reaction to occur and reagents enabling to detect the antigen/antibody complex which has been produced by said immunological reaction.

According to a further aspect, antibodies are provided specifically binding to a polypeptide consisting essentially of a sequence selected from SEQ ID NO: 1-14 or a fragment thereof comprising at least 5 consecutive amino acids derived from SEQ ID NO: 1-14. According to a very specific embodiment, the antibodies do not bind to the full size proteins HLA-A, ribosomal protein S6 and MCM2. According to yet further specific embodiments, the antibodies described herein are specific to polypeptides consisting essentially of a sequence selected from SEQ ID NO: 1-14 or a fragment thereof comprising at least 5 consecutive amino acids derived from SEQ ID NO: 1-14 and do not bind to the cognate full protein.

According to one specific embodiment, an antibody is provided against SEQ ID NO: 1.

As will be clear to the skilled person, the embodiments described herein are not exclusive and can be combined with each other.

FIGURES

FIG. 1: Serological Antigen Selection procedure. The selection procedure entails incubation of phage displaying the RA cDNA library with pooled RA serum (1), leading to formation of phage antigen-IgG complexes (2). These complexes are captured on a solid support by anti-human IgG antibody (3), and non-bound phage are washed away (4). Bound phage are eluted and amplified through infection of host bacteria (5). Phage are produced again and used as input in a subsequent selection round (6).

Figure 2:
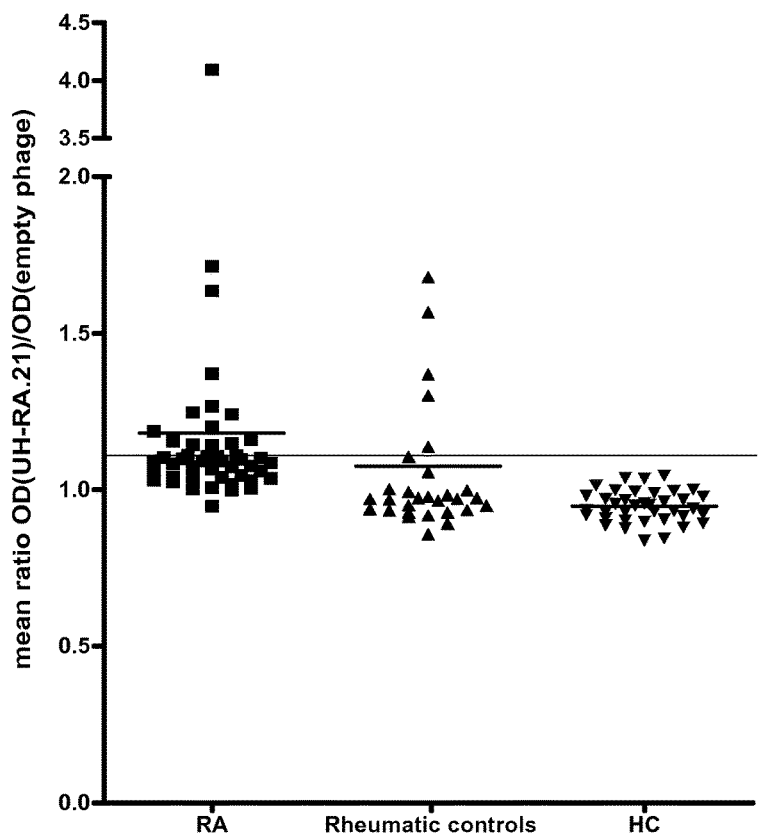
Figure 2:
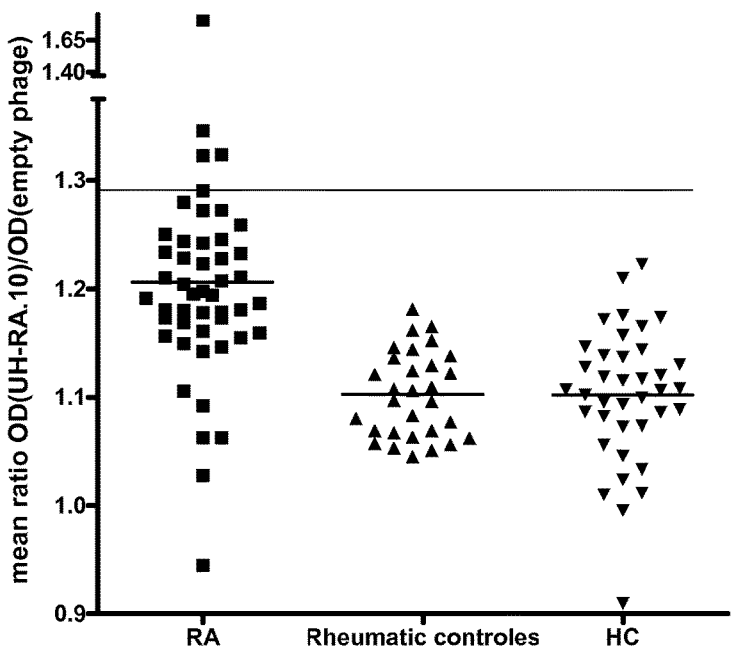

FIG. 2: Antibody levels against UH-RA.21 clone (a) and UH-RA.10 clone (b) in patients with RA, other rheumatic diseases and healthy controls (HC). Scatterplots show mean optical density (OD)(RA-clone):OD(empty phage) ratios of 48 RA patients, 30 patients with other inflammatory rheumatic diseases and 38 healthy controls. Each symbol represents the mean of duplicate or triplicate measurements for each serum sample. The horizontal line constitutes the cut off value for a positive signal, i.e. 3 standard deviation (SD) above the mean OD(phage):OD(empty phage) ratio of the HC group.

a) Antibody levels against UH-RA.21 were significantly higher in RA patients (median 1.09; interquartile range (IQR) 1.04-1.15) than in rheumatic controls (median 0.97; IQR 0.93-1.08), healthy controls (median 0.94; IQR 0.91-0.98), and all controls combined (median 0.96; IQR 0.92-0.99) (p<0.001). b) Antibody levels against UH-RA.10 were significantly higher in RA patients (median 1.20; IQR 1.16-1.25) than in rheumatic controls (median 1.10; IQR 1.07-1.14), healthy controls (median 1.11; IQR 1.07-1.14), and all controls combined (median 1.11; IQR 1.07-1.14) (p<0.001).

Figure 3:
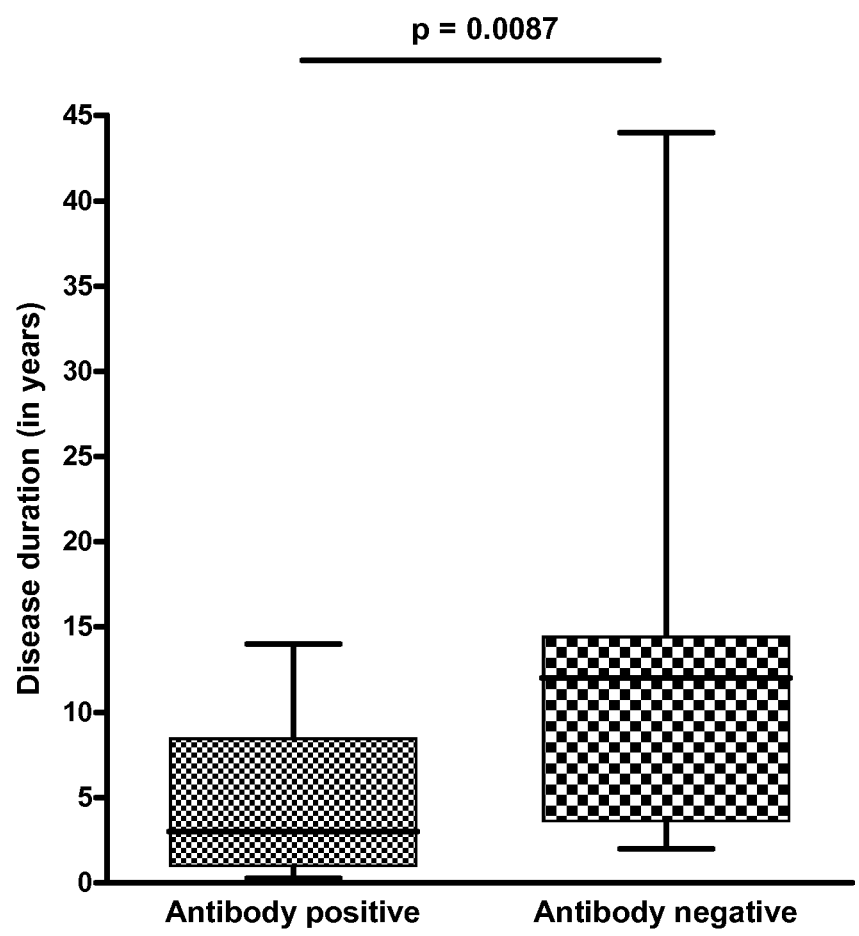
Figure 4A:
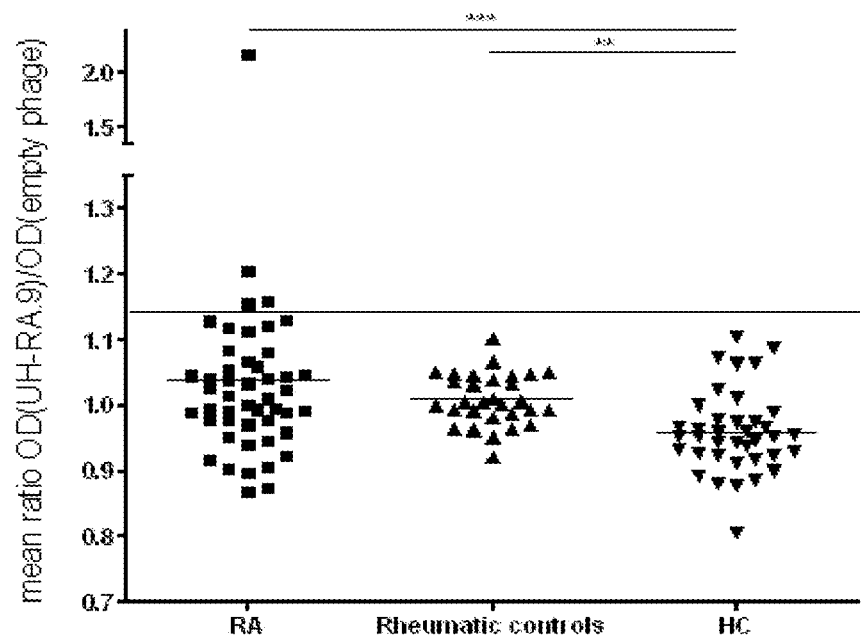
Figure 4B:
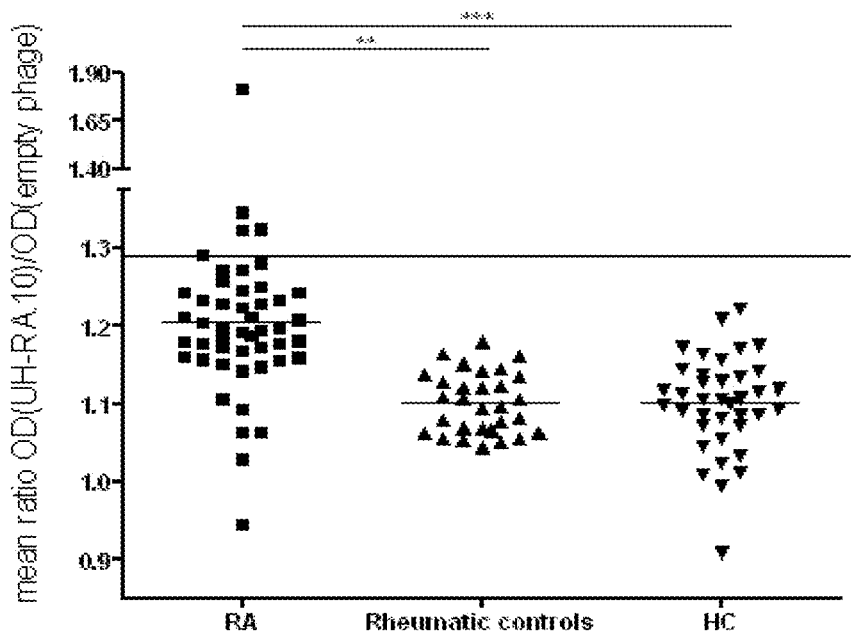
Figure 4C:
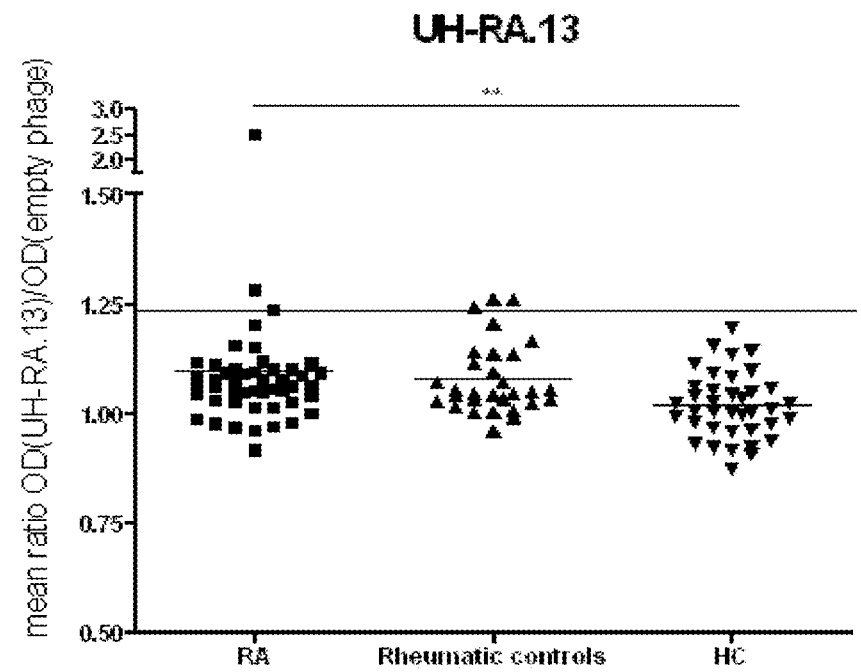
Figure 4D:
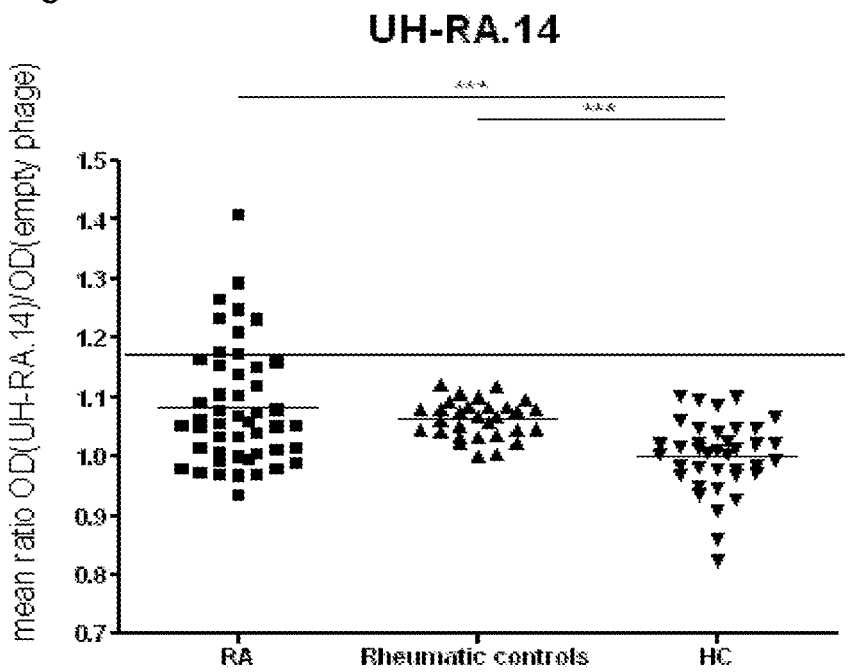
Figure 4E:
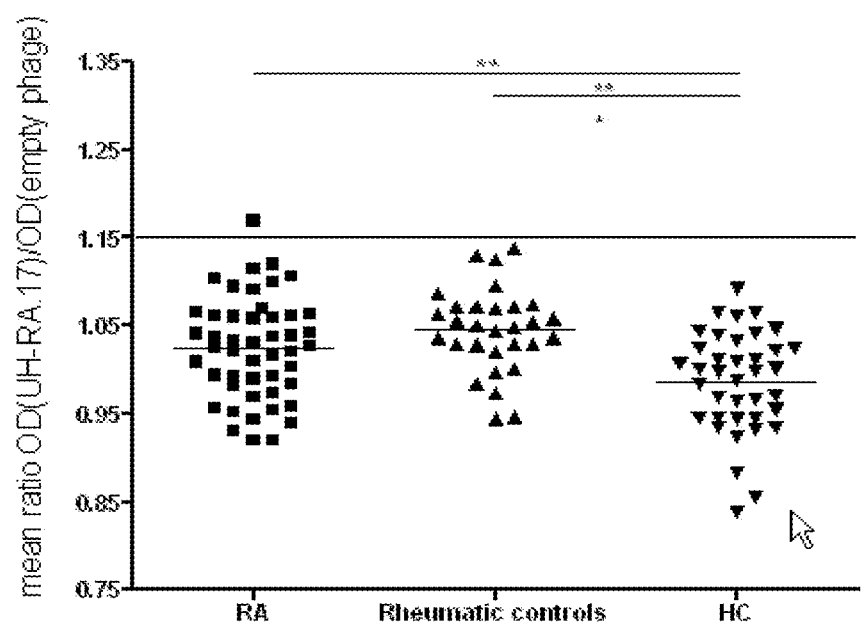
Figure 4F:
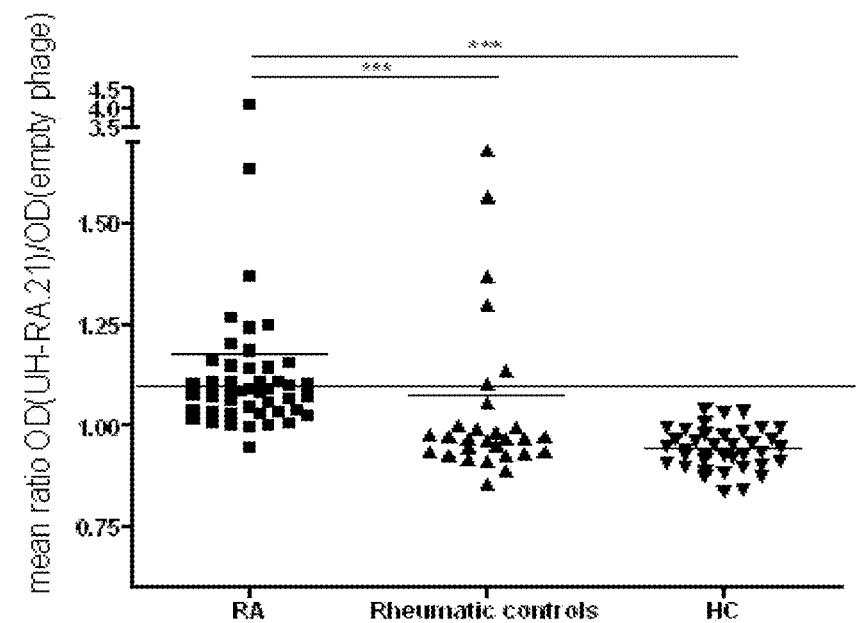
Figure 4G:
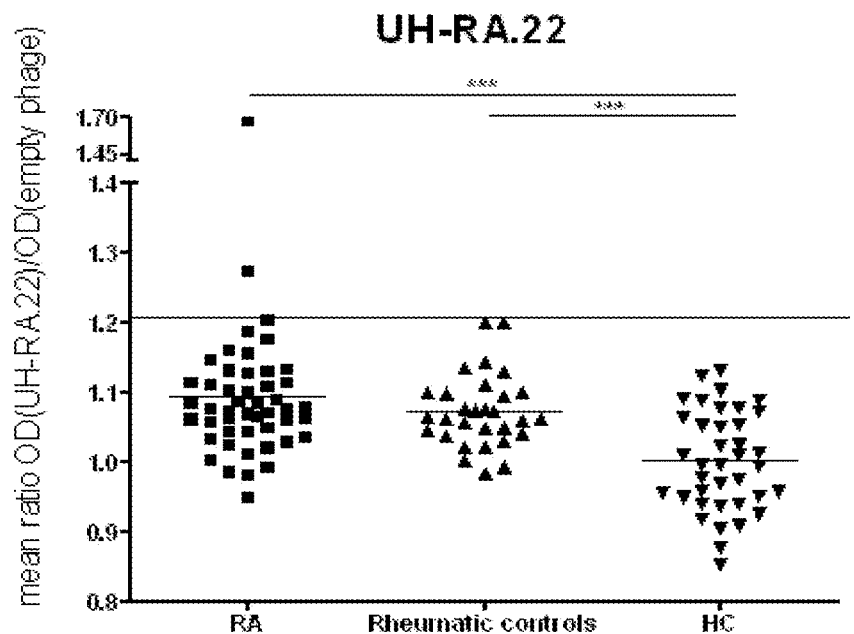
Figure 5A:
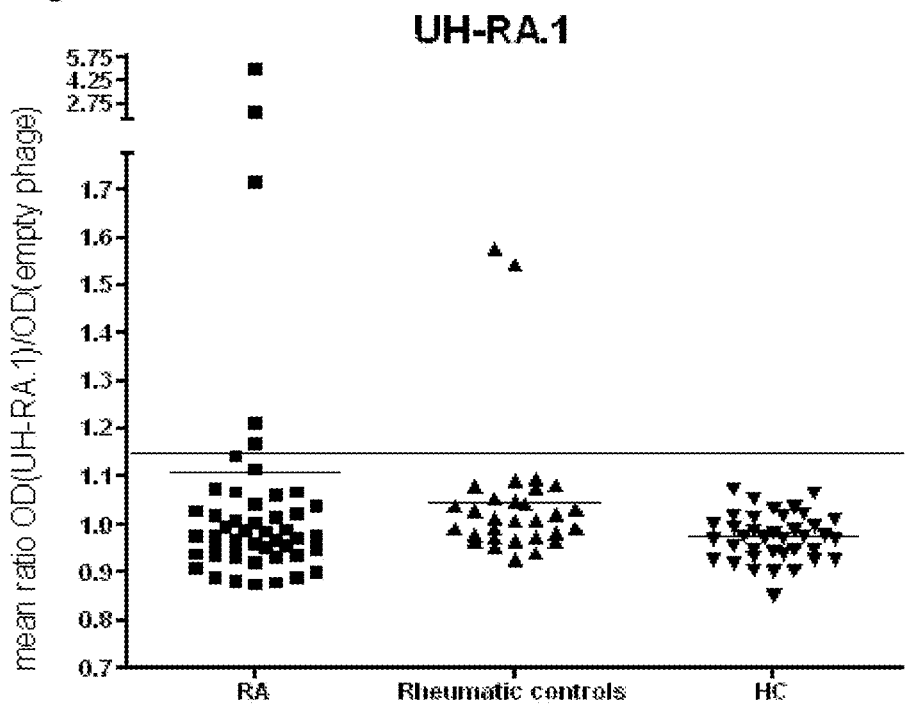
Figure 5B:
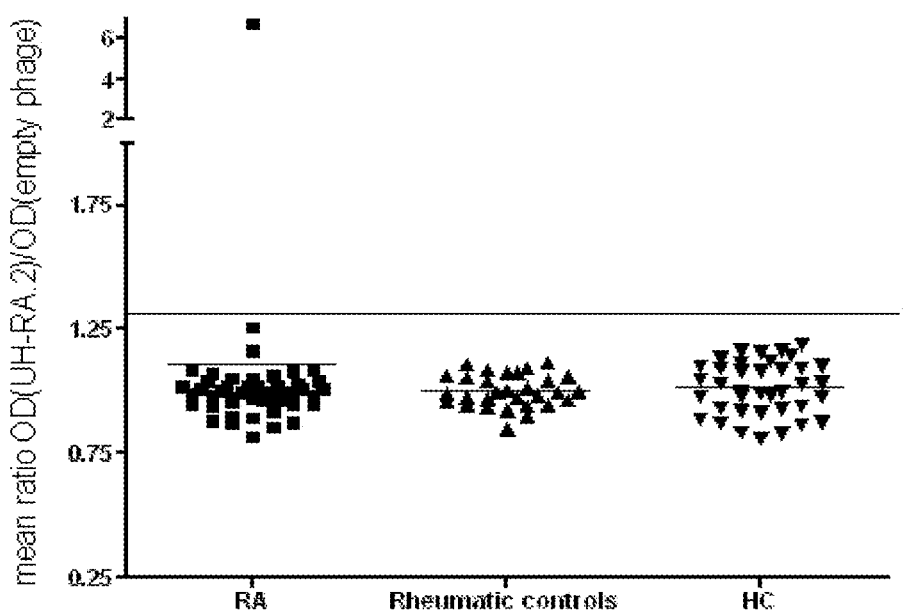
Figure 5C:
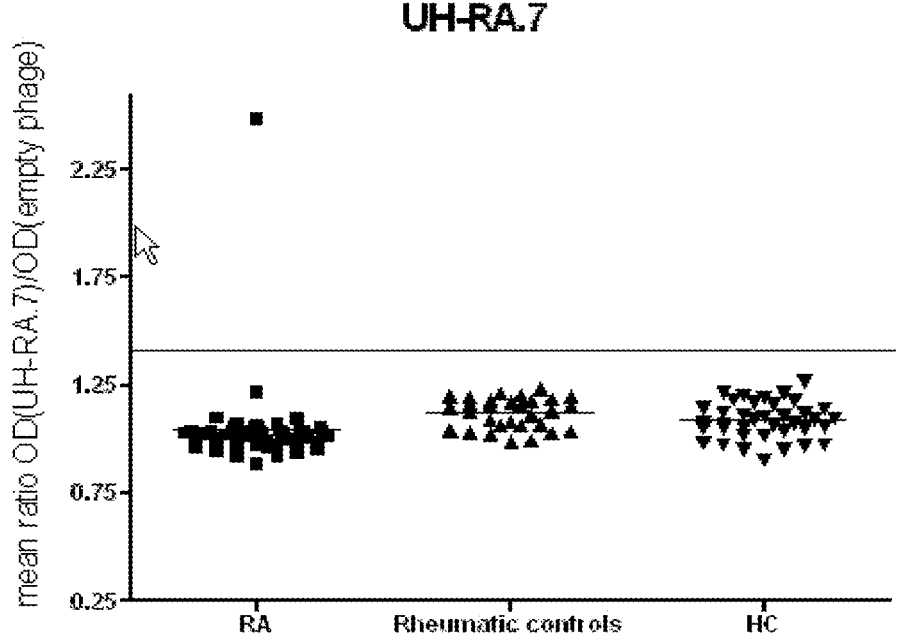
Figure 5D:
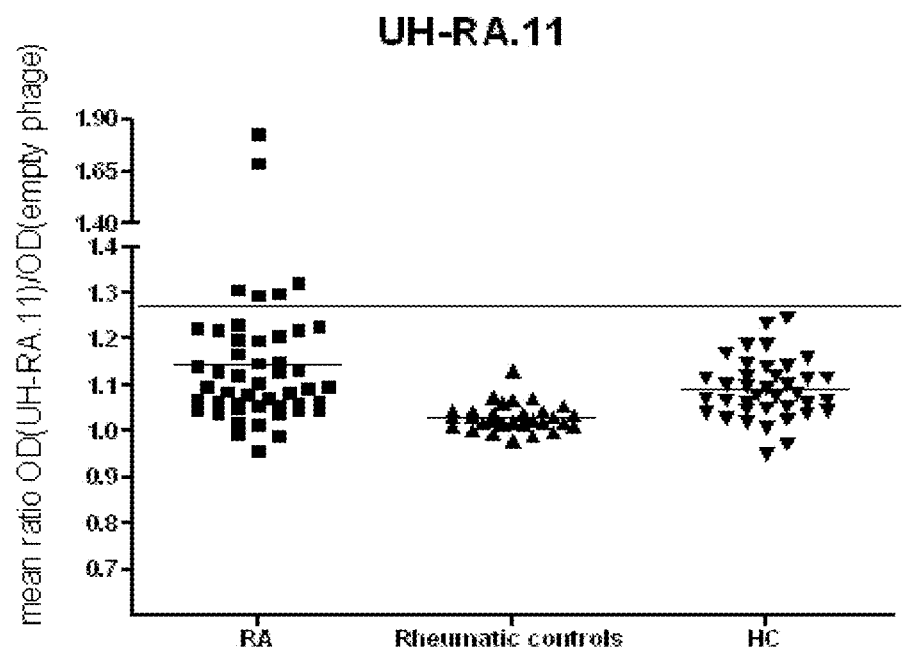
Figure 5E:
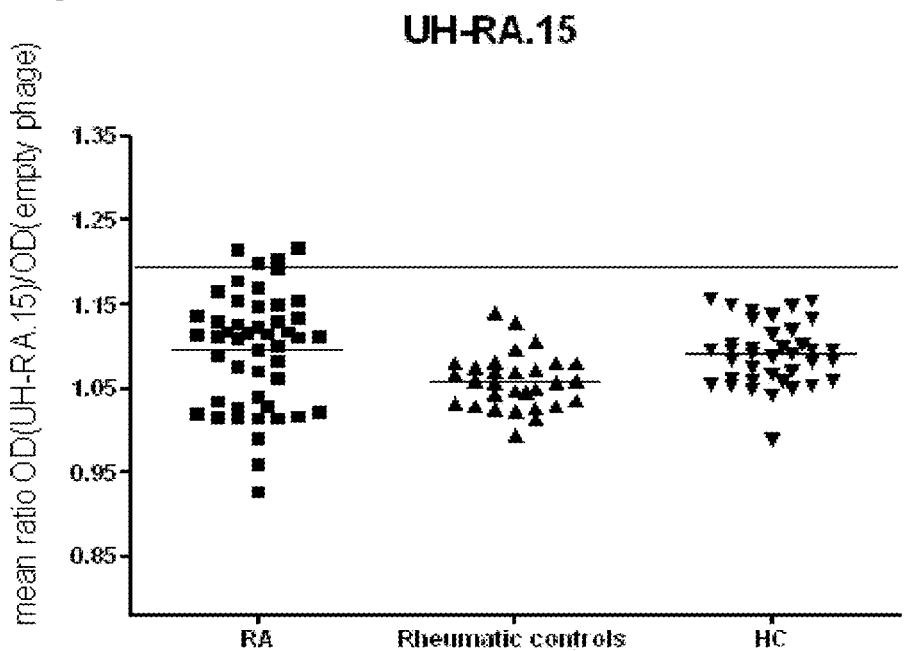
Figure 5F:
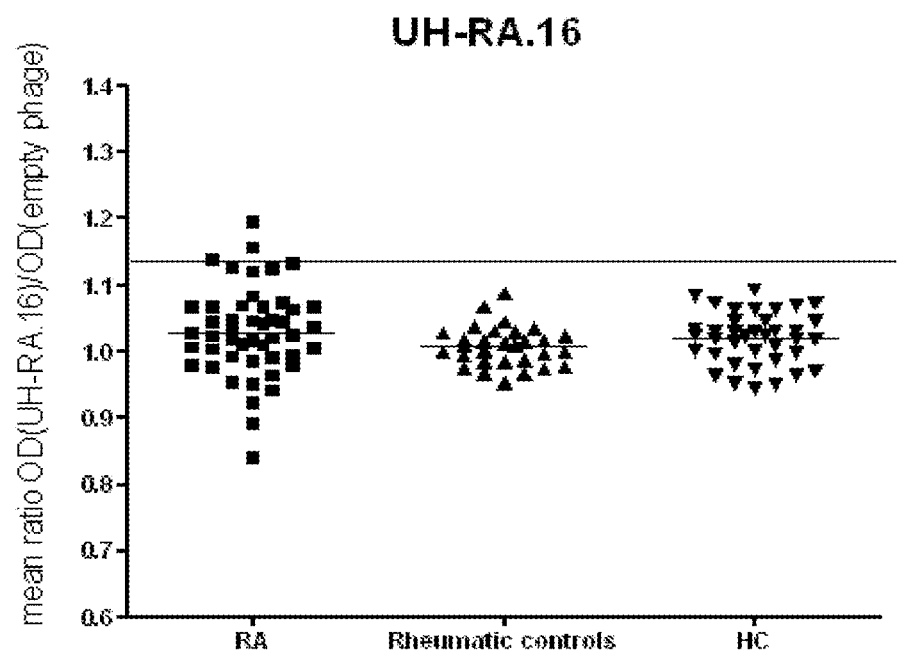
Figure 5G:
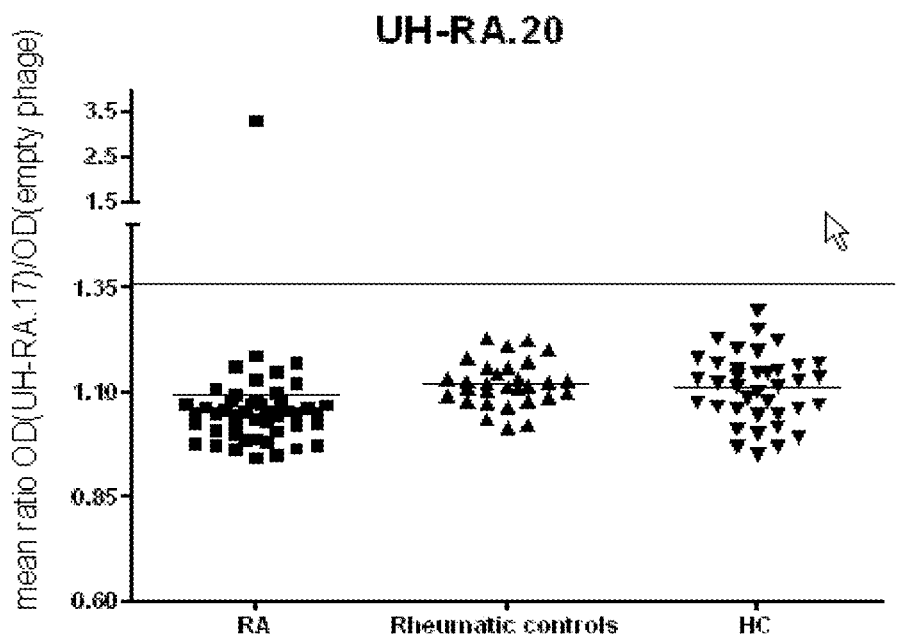

FIG. 3: Relationship between antibody-positivity towards our panel of 14 clones and disease duration. Disease duration of RA patients that are antibody-positive towards our panel is compared with the disease duration of antibody-negative RA patients. Data are represented as scatterplots. A significant association (p=0.0087) was found between antibody-positivity towards at least one of the 14 clones and early disease duration in our RA study population.

FIG. 4: Comparison of antibody levels against identified RA candidate antigens between patients with RA, control patients with other rheumatic diseases and healthy controls (HC). Scatterplots show mean OD(RA-clone)/OD(empty phage) ratios of 48 RA patients, 30 patients with other inflammatory rheumatic diseases and 38 healthy controls. (A) UH-RA.9, (B) UH-RA.10, (C) UH-RA.13, (D) UH-RA.14, (E) UH-RA.17, (F) UH-RA.21, (G) UH-RA.22. Antibody levels against UH-RA.21 and UH-RA.10 were significantly higher in RA patients compared to patients with other rheumatic diseases and healthy controls (P<0.001). Antibody levels against UH-RA.9, UH-RA.13, UH-RA.14, UH-RA.17 and UH-RA.22 were significantly higher in patients with RA compared to the HC group (P<0.001, P<0.01, P<0.001, P<0.001 and P<0.001 respectively). Also, for UH-RA.9, UH-RA.14, UH-RA.17 and UH-RA.22, significant differences in antibody levels between rheumatic control patients and healthy controls were discerned (P<0.01, P<0.001, P<0.001 and P<0.01 respectively). Each symbol represents the mean of triplicate measurements for each serum sample on tested phage and empty phage. The horizontal line constitutes the cut-off value for a positive signal, i.e. 3SD above the mean OD(phage)/OD(empty phage) ratio of the HC group. *P<0.05; P<0.01; *P<0.001.

FIG. 5: Comparison of antibody levels against identified RA candidate antigens between patients with RA, control patients with other rheumatic diseases and healthy controls (HC). Scatterplots show mean OD(RA-clone)/OD(empty phage) ratios of 48 RA patients, 30 patients with other inflammatory rheumatic diseases and 38 healthy controls. (A) UH-RA.1, (B) UH-RA.2, (C) UH-RA.7, (D) UH-RA.11, (E) UH-RA.15, (F) UH-RA.16, (G) UH-RA.20. No significant differences in antibody levels between RA patients, patients with other rheumatic diseases and healthy controls could be discerned. Each symbol represents the mean of triplicate measurements for each serum sample on tested phage and empty phage. The horizontal line constitutes the cut-off value for a positive signal, i.e. 3SD above the mean OD(phage)/OD(empty phage) ratio of the HC group.

Figure 6A:
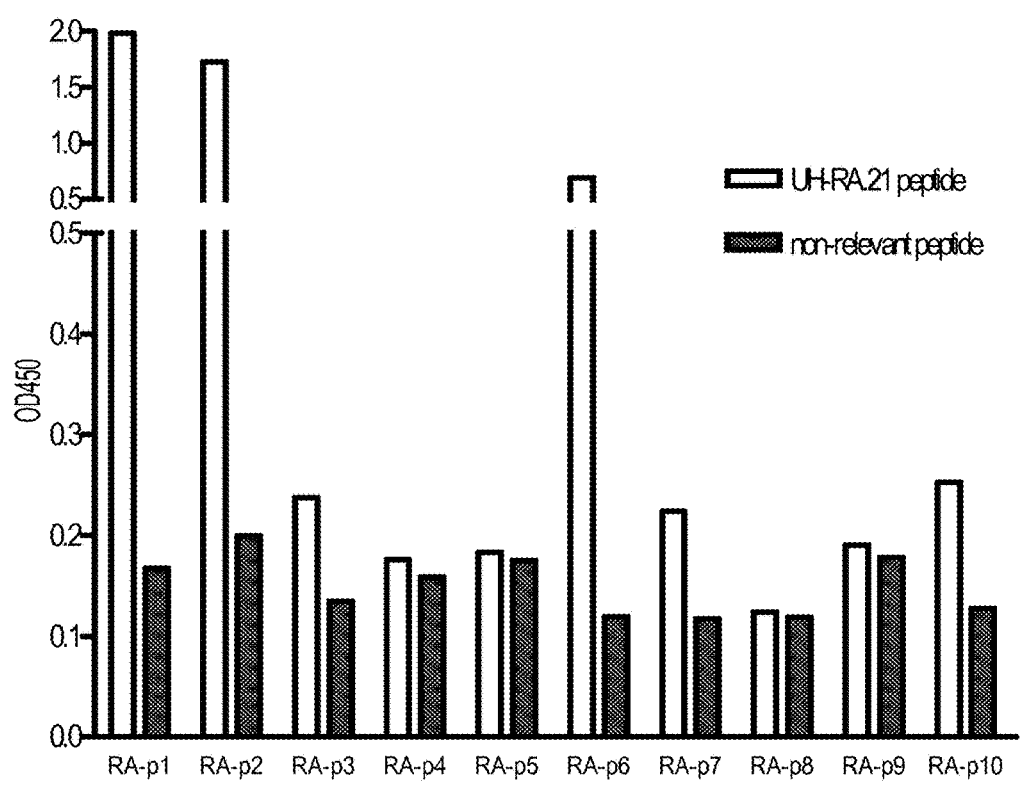
Figure 6B:
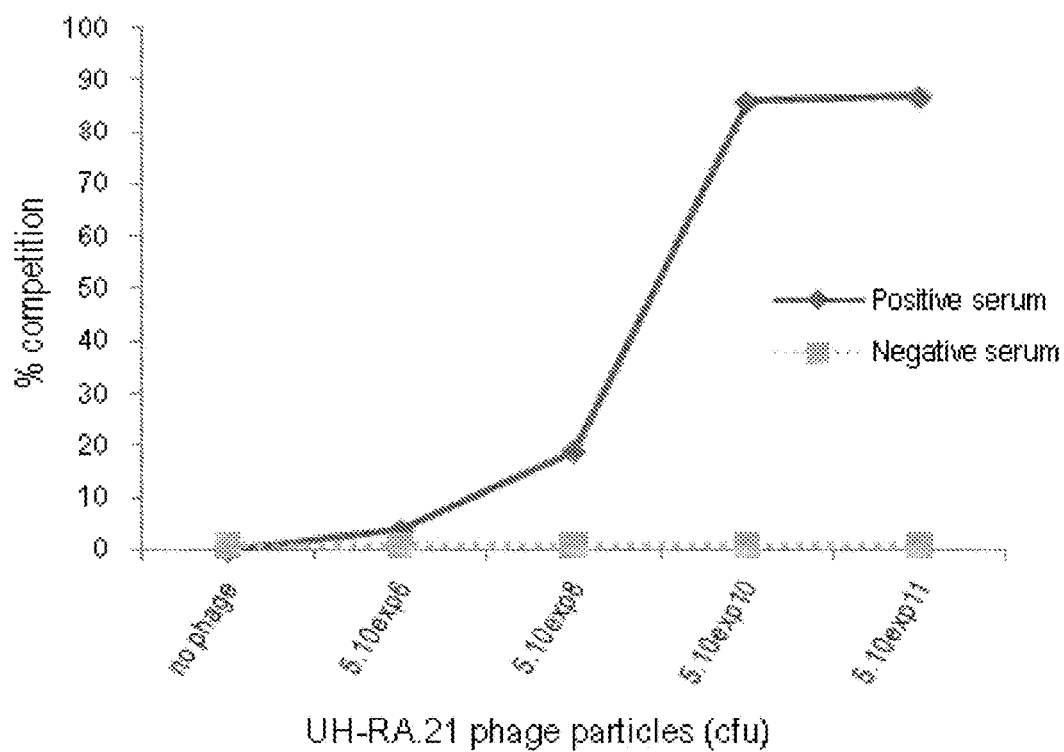
Figure 6C:
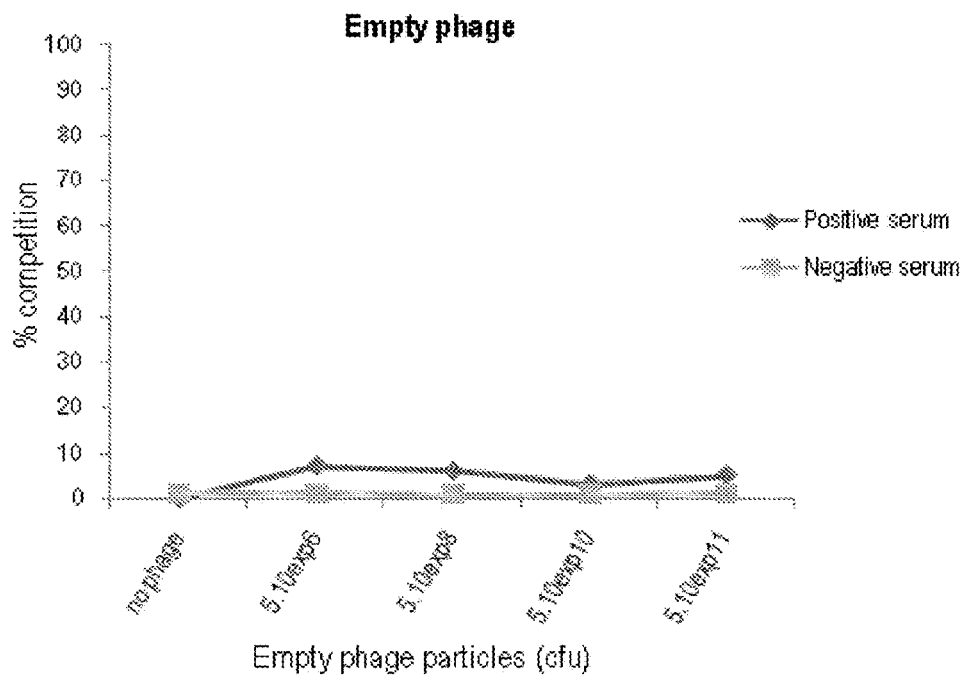

FIG. 6: Specificity of RA immunoreactivity towards displayed cDNA products tested by peptide and competition ELISA. (A) Representative example of reactivity against coated synthetic UH-RA.21 peptide (white bars) in 10 RA samples (RA-p.1 to RA-p.10). As a negative control, serum samples were also incubated with a non-relevant synthetic peptide (black bars). (B) Competition of phage displaying the corresponding UH-RA.21 peptide with coated peptide demonstrated specificity of the serum antibodies against the phage displayed peptide. Increasing amounts of UH-RA.21 phage particles were pre-incubated with anti-UH-RA.21 antibody-positive RA serum (black full line) (determined by phage ELISA), followed by transfer of this mix to coated UH-RA.21 peptide in a synthetic peptide ELISA format. In parallel, an antibody-negative RA serum (dotted line) was pre-incubated with UH-RA.21 displaying phage and was treated in an identical manner as the antibody-positive serum. (C) As a negative control, antibody-positive (black full line) and antibody-negative (dotted line) RA serum samples were pre-incubated with increasing amounts of empty phage particles.

FIG. 7: Results of a synthetic peptide ELISA screening on serum samples from RA patients and different control groups for anti-UH-RA.21 immunoreactivity. Eighteen out of 78 RA patients (23%), 6 out of 49 OA patients (12%), 5 out of 26 psoriatic arthritis patients (19%), 5 out of 35 ankylosing spondylitis patients (14%), 2 out of 48 HC (4%) and 1 out of 42 subjects with mechanical joint complaints (2%) were antibody-positive for UH-RA.21. Significant differences in antibody-reactivity towards UH-RA.21 were demonstrated between RA patients and the combined group of HC and mechanical joint complaints subjects on the one hand, and between RA patients and OA patients on the other hand. The ratios of $OD_{450}$ measured for UH-RA.21 to $OD_{450}$ measured for the non-relevant peptide are shown for all tested patients.

AIMS AND DETAILED DESCRIPTION OF THE INVENTION

Arthritic diseases include both seropositive rheumatoid arthritis (RA) and seronegative chronic arthritis, a prototypic group of autoimmune diseases characterised by non-reactivity of serum antibodies against rheumatoid factor (RF) or citrullinated protein antigens (ACPA). These subtypes include seronegative rheumatoid arthritis (RA), (30% of RA patients remain negative for either RF or ACPA), spondyloarthropathy (SpA), psoriatic arthritis (Psa) and juvenile idiopathic arthritis (JIA). These diseases have a relatively high prevalence (ranging from 1 in 100 for RA), cannot be cured and are associated with high morbidity. In the present invention we have identified a biomarker panel which can be used for the detection of chronic autoimmune arthritis, more specifically for the detection of rheumatoid arthritis (RA) in patients. Biomarkers were isolated with the technology of Serological Antigen Selection (SAS) wherein antigens (i.e. biomarkers) were identified that bind to antibodies present in serum of patients suffering from rheumatoid arthritis. More specifically, a cDNA phage display library comprising cDNA products derived from RA synovial tissue—expressed as a fusion to minor coat protein pVI of filamentous phage M13—was panned to identify cDNA clones that bind auto-antibodies in serum specimens from RA patients. To identify markers for early and RF negative (RF-) ACPA negative (ACPA-) RA, the RA cDNA library was selected on two pools, the first consisting of sera from RA patients with disease duration of less than one year, the second containing sera from RF negative and ACPA negative RA patients. A biomarker panel of 14 antigenic cDNA targets with high specificity for RA was retrieved.

Thus in a first embodiment the invention provides polypeptides (i.e. at least one polypeptide) that can be used as biomarkers or to assist in diagnosis, e.g. of rheumatoid arthritis. Such polypeptide consists essentially of a sequence selected from SEQ ID NO: 1-14 or a fragment thereof comprising at least 5 consecutive amino acids derived from SEQ ID NO: 1-14. Compositions are also provided comprising at least one polypeptide comprising a sequence selected from SEQ ID NO: 1-14 or a fragment thereof comprising at least 5 consecutive amino acids derived from SEQ ID NO: 1-14. In a further specific embodiment, the composition consist essentially of the at least one polypeptide.

Also, a composition is provided comprising at least two different polypeptides comprising a sequence represented by any of SEQ ID NO: 1-14 or a fragment comprising at least 5 consecutive amino acids derived from SEQ ID NO: 1-14. These polypeptides or compositions are herein also designated as a biomarker or as a biomarker panel or as a set of biomarkers. The SEQ ID NO: 1-14 correspond with the translated amino acid sequences of the antigens retrieved by the selection of phage displayed RA cDNA expression library on serum fluid derived from RA patients. The translation of the insert of UH-RA.21 corresponds with SEQ ID NO: 1, that of UH-RA.11 with SEQ ID NO: 2, of UH-RA.14 with SEQ ID NO: 3, of UH-RA.15 with SEQ ID NO: 4, of UH-RA.16 with SEQ ID NO: 5, of UH-RA.1 with SEQ ID NO: 6, of UH-RA.2 with SEQ ID NO: 7, of UH-RA.7 with SEQ ID NO: 8, of UH-RA.9 with SEQ ID NO: 9, of UH-RA.10 with SEQ ID NO: 10, UH-RA.13 with SEQ ID NO: 11, of UH-RA.17 with SEQ ID NO: 12, of UH-RA.20 with SEQ ID NO: 13, and the translation of the insert of UH-RA.22 corresponds with SEQ ID NO: 14 (see table 7). The nucleotide sequences which encode SEQ ID NO: 1-14 are depicted in SEQ ID NO: 15-28 (wherein SEQ ID NO: 15 encodes SEQ ID NO: 1, . . . , and SEQ ID NO: 28 encodes SEQ ID NO: 14). As is clear to the skilled person, one or more nucleic acids of the invention (SEQ ID NO: 15-28) may also be used as a biomarker, e.g. by having them transcribed or translated; or by detecting the nucleic acids directly instead of detecting the proteins, e.g. via quantitative PCR.

Thus a composition comprises at least one polypeptide, or possibly at least two polypeptides, wherein such a polypeptide comprises a sequence as depicted by SEQ ID NO: 1, 2, 3, 4, 5, 6, 7, 8, 9, 10, 11, 12, 13 or 14. This means that a polypeptide present in the composition can also be a protein, particularly when the composition contains at least two polypeptides. As an example SEQ ID NO: 12 was cloned as a partial 76 amino acid fragment of Selenoprotein P (protein product as detected using SAS). Since SEQ ID NO: 12 (corresponding with UH-RA.17) is a fragment of the selenoprotein P protein the composition can also comprise the full length selenoprotein P protein. The composition of the invention can also comprise at least one, or at least two different, polypeptide(s) wherein said polypeptide(s) are fragments comprising at least 5 consecutive amino acids derived from SEQ ID NO: 1, 2, 3, 4, 5, 6, 7, 8, 9, 10, 11, 12, 13 or 14. It is envisaged that 5 consecutive amino acids derived from SEQ ID NO: 1-14 are sufficient to be recognized as antigens by the auto-antibodies present in for example blood serum or blood plasma.

According to further particular embodiments, the fragments of the polypeptides comprise at least 6 consecutive amino acids derived from SEQ ID NO: 1-14, or at least 7, at least 8, at least 9, at least 10, at least 11, at least 12, at least 13, at least 14, at least 15 or at least 20 amino acids derived from SEQ ID NO: 1-14.

According to a specific embodiment, the polypeptide sequences used are not completely identical to SEQ ID NO: 1-14, but almost identical. For instance, they show 99% sequence identity, 98% sequence identity, 95% sequence identity, 90% sequence identity, or 85% sequence identity to any of SEQ ID NO: 1-14. Percentage sequence identity is calculated according to methods known in the art, e.g. the BLAST algorithm. The following terms are typically used to describe the sequence relationships between two or more nucleic acids or polynucleotides: (a) "reference sequence", (b) "comparison window", and (c) "percentage of sequence identity".

(a) As used herein, "reference sequence" is a defined sequence used as a basis for sequence comparison. A reference sequence may be a subset or the entirety of a specified sequence; for example, SEQ ID NO:1 or a fragment of at least 5 consecutive amino acids thereof.

(b) As used herein, "comparison window" makes reference to a contiguous and specified segment of a polynucleotide or amino acid sequence, wherein the polynucleotide or amino acid sequence may be compared to a reference sequence and wherein the portion of the polynucleotide or amino acid sequence in the comparison window may comprise additions or deletions (i.e., gaps) compared to the reference sequence (which does not comprise additions or deletions) for optimal alignment of the two sequences. Those of skill in the art understand that to avoid a high similarity to a reference sequence due to inclusion of gaps in the polynucleotide or amino acid sequence, a gap penalty is typically introduced and is subtracted from the number of matches. Note that to align sequences dissimilar in length, the comparison window will usually be determined using the shorter of the two sequences.

(c) As used herein, "percentage of sequence identity" means the value determined by comparing two optimally aligned sequences over a comparison window, wherein the portion of the polynucleotide or amino acid sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base or amino acid occurs in both sequences to yield the number of matched positions, dividing the number of matched positions by the total number of positions in the window of comparison and multiplying the result by 100 to yield the percentage of sequence identity.

Methods of aligning sequences for comparison are well known in the art. Gene comparisons can be determined by conducting BLAST (Basic Local Alignment Search Tool; Altschul, S. F., et al., (1993) J. Mol. Biol. 215:403-410; see also, www.ncbi.nlm.nih.gov/BLAST/) searches under default parameters for identity to sequences contained in the BLAST "GENEMBL" database.

According to a specific embodiment, the polypeptide sequences used are not completely identical to SEQ ID NO: 1-14, but highly similar, i.e. amino acids have been conservatively substituted. This implies that one or more hydrophobic amino acids have been replaced with other hydrophobic amino acids (or vice versa for hydrophilic amino acids), one or more positively charged amino acids have been replaced with other positively charged amino acids (or vice versa for negatively charged amino acids), and so on. Percentage similarity can be determined by the skilled person, e.g. using the BLAST program. In particular, the sequences used are 99% similar, 98% similar, 97% similar, 95% similar, 90% similar or 85% similar to any one of SEQ ID NO: 1-14.

In a particular embodiment the composition comprises 14 different polypeptides comprising a sequence selected from SEQ ID NO: 1-14 or 14 different fragments comprising at least 5 consecutive amino acids derived from SEQ ID NO: 1-14.

In another embodiment the invention provides the use of a composition of the invention for detecting the presence of specific antibodies to at least one polypeptide present in said composition wherein said antibodies are present in a body fluid of a mammal.

In another particular embodiment the invention provides the use of a composition of the invention for detecting the presence of specific auto-antibodies to at least one polypeptide present in said composition wherein said auto-antibodies are present in a body fluid of a mammal.

In particular embodiments said use of a composition is an "in vitro" use of a composition. The latter implies a diagnostic method with no direct interaction with the patient. In still another embodiment the invention provides the use of a composition of the invention for the manufacture of a diagnostic assay to detect autoimmune disorders, more specifically to the diagnosis of rheumatoid disorders, chronic autoimmune arthritis and even more specifically to the diagnosis of rheumatoid arthritis.

The term 'body fluid' includes blood, blood serum, blood plasma, saliva, urine, tears, bone marrow fluid, cerebrospinal fluid (CSF), synovial fluid, lymphatic fluid, amniotic fluid, nipple aspiration fluid and the like. Preferred body fluids for analysis are those that are conveniently obtained from patients, particularly preferred body fluids include blood serum, blood plasma and synovial fluid.

In yet another embodiment the invention provides a method for detecting rheumatoid arthritis in a mammal comprising i) detecting the presence of at least one antibody in a body fluid derived from said mammal wherein said antibody has a specificity for a polypeptide comprising a sequence selected from the group consisting of SEQ ID NO: 1-14 or a fragment comprising at least 5 consecutive amino acids derived from SEQ ID NO: 1-14 and wherein ii) the presence of said antibody indicates that said mammal suffers from rheumatoid arthritis.

In yet another embodiment the invention provides a method for detecting rheumatoid arthritis with a disease stage of less than one year.

In yet another embodiment the invention provides a method for detecting rheumatoid arthritis in a body fluid derived from a mammal which is seronegative for rheumatoid factor and/or anti-CCP antibodies.

In yet another embodiment the method for detecting rheumatoid arthritis in a mammal of the present invention is combined with the detection of rheumatoid factor, citrullinated peptides (e.g. U.S. Pat. No. 6,858,438, WO2007017556), a combination between rheumatoid factor and citrullinated peptides, citrullinated peptides and interleukin-6 as in WO2005064307, or still other antigens such as for example described in U.S. Pat. No. 5,585,464, U.S. Pat. No. 5,888,833 and WO0146222).

In yet another embodiment the invention provides a method for evaluating the prognosis/disease severity of rheumatoid arthritis in a mammal comprising i) detecting the presence or quantity of at least one antibody in a body fluid derived from said mammal wherein said antibody has a specificity for a polypeptide comprising a sequence selected from the group consisting of SEQ ID NO: 1-14 or a fragment comprising at least 5 consecutive amino acids derived from SEQ ID NO: 1-14 and wherein ii) the presence (decreased or increased) concentration of said antibody indicates the prognosis of rheumatoid arthritis in said mammal.

In yet another embodiment the invention provides a method for selecting mammals for a specific therapeutic treatment of rheumatoid arthritis or evaluating the therapeutic treatment of rheumatoid arthritis in a mammal comprising i) detecting the presence or quantity of at least one antibody in a body fluid derived from said mammal wherein said antibody has a specificity for a polypeptide comprising a sequence selected from the group consisting of SEQ ID NO: 1-14 or a fragment comprising at least 5 consecutive amino acids derived from SEQ ID NO: 1-14 and wherein ii) the presence or increased concentration of said antibody leads to an election of a specific therapeutic treatment of rheumatoid arthritis in said mammal.

In a preferred embodiment said body fluid is serum, plasma or synovial fluid.

In another preferred embodiment said mammal is a human.

In yet another embodiment the invention provides an antibody that specifically binds to a polypeptide selected from the group consisting of polypeptides represented by SEQ ID NO: 1-14. Methods for generating antibodies are well known in the art. In a preferred embodiment the antibodies are monoclonal antibodies. For the purpose of generation of antibodies the polypeptides forming part of the compositions of the invention may be synthesized chemically or may be made in a recombinant way. They may also be coupled to a soluble carrier after synthesis or after recombinant production. If a carrier is used the nature of such a carrier should be such that it has a molecular weight greater than 5000 and should not be recognized by antibodies. Such a carrier can be a protein. Proteins which are frequently used as carriers are keyhole limpet hemocyanin, bovine gamma globulin, bovine serum albumin, and poly-L-lysine. There are many well described techniques for coupling peptides to carriers. The linkage may occur at the N-terminus, C-terminus or at an internal site in the peptide. The polypeptide may also be derivatized for coupling. The polypeptides may also be synthesized directly on an oligolysine core in which both the alpha as well as the epsilon-amino groups of lysines are used as growth points for the polypeptides. The number of lysines comprising the core is preferably 3 or 7. Additionally, a cysteine may be included near or at the C-terminus of the complex to facilitate the formation of homo- or heterodimers.

In general terms the invention relates to a process for detecting antibodies (i.e. auto-antibodies) related to RA or other rheumatic/autoimmune disorders in a biological sample (such as serum or plasma) of a mammal liable to contain them, this process comprising contacting the biological sample with a composition according to the invention under conditions enabling an immunological reaction between said composition and the antibodies which are possibly present in the biological sample and the detection of the antigen/antibody complex which may be formed. The detection can be carried out according to any classical process. By way of examples immune-enzymatic processes according to the ELISA technique or immunofluorescent or radioimmunological (RIA) or the equivalent ones can be used. Thus the invention also relates to polypeptides according to the invention labeled by an appropriate label of the enzymatic, fluorescent, biotin, radioactive type. Such a method for detecting antibodies related to RA comprises for instance the following steps: deposit of determined amounts of a polypeptidic composition according to the invention on a support (e.g. into wells of a titration microplate), introduction on said support (e.g. into wells) of increasing dilutions of the body fluid (e.g. serum) to be diagnosed, incubation of the support (e.g. microplate), repeated rinsing of the support (e.g. microplate), introduction on the support labeled antibodies which are specific for immunoglobulins present in the body fluid, the labeling of these antibodies being based on the activity of an enzyme which is selected from among the ones which are able to hydrolyze a substrate by modifying the absorption of the radiation of this latter at least at a given wave length, detection by comparing with a control standard of the amount of hydrolyzed substrate.

In yet another embodiment the invention also relates to a process for detecting and identifying antigens of RA in a body specimen (tissue, biopsy, . . . ) liable to contain them, this process comprising: contacting the biological sample with an appropriate antibody of the invention (i.e. antibodies with a specificity for a polypeptide of the composition) under conditions enabling an immunological reaction between said antibody and the antigens of RA which are possibly present in the biological sample and the detection of the antigen/antibody complex which may be formed.

Thus antibodies, in particular auto-antibodies, which recognize the polypeptides of the invention, can be detected in a variety of ways. One method of detection is further described in the examples and uses enzyme-linked immunosorbant assay (ELISA) of the polypeptides of the invention displayed by phages (i.e. phage-ELISA technology). The latter technology is fully described in Somers V. et al (2005) *J. of Autoimmunity* 25: 223-228, wherein paragraph 2.6 on page 225 is herein specifically incorporated), In other ways in the detection in ELISA a polypeptide or a mixture of polypeptides is bound to a solid support. In some cases, this will be a microtiter plate but may in principle be any sort of insoluble solid phase (e.g. glass, nitrocellulose). In one embodiment a suitable dilution or dilutions of for example serum to be tested is brought into contact with the solid phase to which the polypeptide is bound. In another embodiment "a solution hybridization" is carried out in which high affinity interactions occur (eg. biotinylated polypeptides of the composition are pre-incubated with serum). The incubation is carried out for a time necessary to allow the binding reaction to occur. Subsequently, unbound components are removed by washing the solid phase. The detection of immune complexes (i.e. auto-antibodies present in for example human serum binding to at least one polypeptide of the invention) is achieved using antibodies which specifically bind to human immunoglobulins, and which have been labeled with an enzyme, preferably but not limited to either horseradish peroxidase, alkaline phosphatase, or beta-galactosidase, which is capable of converting a colorless or nearly colorless substrate or co-substrate into a highly colored product or a product capable of forming a colored complex with a chromogen. Alternatively, the detection system may employ an enzyme which, in the presence of the proper substrate(s), emits light. The amount of product formed is detected either visually, spectrophotometrically, electrochemically, fluorescently or luminometrically, and is compared to a similarly treated control. The detection system may also employ radioactively labeled antibodies, in which case the amount of immune complex is quantified by scintillation counting or gamma counting. Other detection systems which may be used include those based on the use of protein A derived from *Staphylococcus aureus* Cowan strain I, protein G from group C *Staphylococcus* sp. (strain 26RP66), or systems which make use of the high affinity biotin-avidin or streptavidin binding reaction.

The polypeptides of the invention may be either labeled or unlabeled. Labels which may be employed may be of any type, such as enzymatic, chemical, fluorescent, luminescent, or radioactive. In addition, the polypeptides may be modified for binding to surfaces or solid phases, such as, for example, microtiter plates, nylon membranes, glass or plastic beads, and chromatographic supports such as cellulose, silica, or agarose. The methods by which polypeptides can be attached or bound to solid support or surface are well known to those skilled in the art.

The polypeptides of the invention can be prepared according to the classical techniques in the field of peptide synthesis. The synthesis can be carried out in homogeneous solution or in solid phase. For instance, the synthesis technique in homogeneous solution which can be used is the one described by Houbenweyl in the book titled "Methode der organischen chemie" (Method of organic chemistry) edited by E. Wunsh, vol. 15-I et II. THIEME, Stuttgart 1974. The polypeptides of the invention can also be prepared in solid phase according to the method described by Atherton & Shepard in their book titled "Solid phase peptide synthesis" (Ed. IRL Press, Oxford, N.Y., Tokyo, 1989). Synthesis protocols in the art generally employ the use of t-butyloxycarbonyl- or 9-fluorenylmethoxy-carbonyl-protected activated amino acids. The procedures for carrying out the syntheses, the types of side-chain protection, and the cleavage methods are amply described in, for example, Stewart and Young, Solid Phase Peptide Synthesis, 2nd Edition, Pierce Chemical Company, 1984; and Atherton and Sheppard, Solid Phase Peptide Synthesis, IRL Press, 1989.

In yet another embodiment antibodies raised to polypeptides of the invention (or carrier-bound polypeptides) can also be used in conjunction with labeled polypeptides of the invention for the detection of (auto)-antibodies present in for example serum by competition assay. In this case, antibodies raised to polypeptides are attached to a solid support which may be, for example, a plastic bead or a plastic tube. Labeled polypeptide is then mixed with suitable dilutions of the fluid (e.g. serum) to be tested and this mixture is subsequently brought into contact with the antibody bound to the solid support. After a suitable incubation period, the solid support is washed and the amount of labeled polypeptide is quantified. A reduction in the amount of label bound to the solid support is indicative of the presence of (auto)-antibodies in the original sample. By the same token, the polypeptide may also be bound to the solid support. Labeled antibody may then be allowed to compete with (auto)-antibody present in the sample (e.g. serum) under conditions in which the amount of polypeptide is limiting. As in the previous example, a reduction in the measured signal is indicative of the presence of (auto)-antibodies in the sample tested.

In a particular embodiment a test for giving evidence of the fact that one or more polypeptides present in a composition of the invention are recognized by antibodies present in for example serum (for example auto-antibodies present in serum of rheumatoid arthritis patients) is an immunoblotting (or Western blotting) analysis or LINE assay. In the latter case polypeptides can be chemically synthesized or polypeptides (or the protein) can be produced via recombinant techniques. In short, after sodium dodecyl sulfate-polyacrylamide gel electrophoresis, polypeptides of the invention are blotted onto nitrocellulose membranes (e.g. Hybond C. (Amersham)) as described by Towbin H. et al., 1979, "Electrophoretic transfer of proteins from polyacrylamide gels to nitrocellulose sheets: procedure and some applications", Proc. Natl. Acad. Sci. USA 76:4350-4354. In order to identify selective recognition of polypeptides (or proteins) of the invention by serum, nitrocellulose sheets are incubated overnight with each of these samples (e.g. diluted 1:50) (after blocking a-specific protein-binding sites). Reactive areas on the nitrocellulose sheets are revealed by incubation with e.g. peroxidase conjugated goat anti-human immunoglobulin G antibody (e.g. diluted 1:200) for 4 h, and after repeated washings, color reaction is developed by adding for example alpha-chloronaphtol (Bio-Rad Laboratories, Richmond, Calif.) in the presence of hydrogen peroxide.

It goes without saying that the free reactive functions which are present in some of the amino acids, which are part of the constitution of the polypeptides of the invention, particularly the free carboxyl groups which are carried by the groups Glu and Asp or by the C-terminal amino acid on the one hand and/or the free NH2 groups carried by the N-terminal amino acid or by amino acids inside the peptidic chain, for instance Lys, on the other hand, can be modified in so far as this modification does not alter the above mentioned properties of the polypeptide. The polypeptides which are thus modified are naturally part of the invention. The above mentioned carboxyl groups can be acylated or esterified. Other modifications are also part of the invention. Particularly, the amine or carboxyl functions or both of terminal amino acids can be themselves involved in the bond with other amino acids. For instance, the N-terminal amino acid can be linked to the C-terminal amino acid of another peptide comprising from 1 to several amino acids.

Furthermore, any peptidic sequences resulting from the modification by substitution and/or by addition and/or by deletion of one or several amino acids of the polypeptides according to the invention are part of the invention in so far as this modification does not alter the above mentioned properties of said polypeptides. The polypeptides according to the invention can be glycosylated or not, particularly in some of their glycosylation sites of the type Asn-X-Ser or Asn-X-Thr, X representing any amino acid.

An advantageous recombinant polypeptide included in the composition of the invention is SEQ ID NO: 1 (UH-RA.21) since this polypeptide shows the highest frequency of antibody responses in serum of RA patients.

Variations of these polypeptides are also possible depending on its intended use. For example, if the polypeptide is to be used to raise antisera, the polypeptide may be synthesized with an extra cysteine residue added. This extra cysteine residue is preferably added to the amino terminus and facilitates the coupling of the polypeptide to a carrier protein which is necessary to render the small polypeptide immunogenic. If the polypeptide is to be labeled for use in radioimmune assays, it may be advantageous to synthesize the protein with a tyrosine attached to either the amino or carboxyl terminus to facilitate iodination. This polypeptide possesses therefore the primary sequence of the polypeptide above-mentioned but with additional amino acids which do not appear in the primary sequence of the protein and whose sole function is to confer the desired chemical properties to the polypeptide.

In yet another embodiment the invention provides for a kit to diagnose RA. To carry out the diagnostic method for RA, the following necessary or kit can be used, said necessary or kit comprising: a composition (comprising at least one polypeptide selected from SEQ ID NO: 1-14) according to the invention, or at least one fragment comprising at least 5 consecutive amino acids derived from SEQ ID NO: 1-14, reagents for making a medium appropriate for the immunological reaction to occur, reagents enabling to detect the antigen/antibody complex which has been produced by the immunological reaction, said reagents possibly having a label, or being liable to be recognized by a labeled reagent, more particularly in the case where the above mentioned polypeptide is not labeled.

Other characteristics and advantages of the invention will appear in the following examples and the figures illustrating the invention.

EXAMPLES

1. Construction of a RA cDNA Phage Display Library

The RA synovial tissue used for library construction was analysed immunohistochemically prior to use. Severe and ongoing inflammation was shown by the presence of inflammatory infiltrates consisting primarily of macrophages and T-lymphocytes. B-lymphocytes were less prominent and primarily localised perivascularly. No germinal center structures were detected. Primary library construction into the λ-Uni-ZAP XR vector resulted in the generation of a RA λ-Uni-ZAP XR library with a primary diversity of $4.5 \times 10^6$ recombinants. After mass excision, restriction enzyme digestion and directional cloning into our phagemid vectors, we obtained RA-pSPVI-A/B/C display libraries containing respectively $4.6 \times 10^6$, $8.5 \times 10^6$ and $5.3 \times 10^6$ cfu. Sequencing of the resulting RA-pSPVI libraries showed the presence of cDNA sequences encoding known synovial and cartilage components (collagen, osteonectin), candidate RA antigens (for example fibronectin), and unknown genes.

2. Affinity Selection of a RA cDNA Phage Display Library

To enrich the RA cDNA phage display library for cDNA products recognized specifically by IgG present in the serum of early and RF− ACPA− RA patients, successive selection rounds were performed with an early RA serum pool and a RF− ACPA− RA serum pool. An outline of the SAS procedure is given in FIG. 1. Phage displaying the RA cDNA expression library were incubated with pooled RA serum, resulting in the formation of antigen-antibody complexes between RA IgG and their target antigens displayed at the surface of the phage. After retention of these phage-IgG complexes, output phage were amplified in host bacteria and used as input in a subsequent selection round. By repeating this cycle of affinity selection and amplification on the RA phage display library with RA serum, phage displaying RA targets will be enriched. Moreover, as affinity selection occurred in a solution phase format, preferential selection of high-affinity phage-antibody interactions would be expected.

For both serum pools, 4 consecutive selection rounds on the RA phage display library were performed. The extent of phage enrichment was monitored throughout the selection procedure by determination of the ratio of output phage to input phage titer (output:input ratio). As shown in table 4, the phage output:input ratio rises with increasing rounds of selection for both RA serum pools, indicating specific enrichment of phage. The small decrease in phage output:input titer for round 2 compared to the first round can be explained by an increase in selection stringency from the first round onward.

3. Screening for Enrichment of Output Phage

To identify phage clones that were enriched by applying affinity selection rounds with the two RA serum pools, colony PCR and DNA fingerprinting techniques were performed on output phage from selection rounds 2, 3 and 4. Application of these techniques generates characteristic restriction profiles for each cDNA clone. The increasing presence of a particular restriction profile with increasing selection round number indicates enrichment of this particular cDNA clone throughout the selection procedure. In total, 250 phage clones obtained from selections on both serum pools (selection rounds 2, 3 and 4) were screened by colony PCR and fingerprinting analysis (table 1). While the output phage from the second round still showed a high degree of diversity, from the third round on however, specific fingerprinting profiles became more prominent, indicating enrichment of specific clones (data not shown). In the fourth round only a limited number of fingerprinting patterns could be discerned, indicative of dominant enrichment of a few phage clones. The screening resulted in the identification of 22 enriched cDNA clones that were annotated with the name UH-RA.number, which is short for RA.clone number (table 5). Eleven enriched cDNA clones (UH-RA.1-UH-RA.11) were obtained from selections on the early RA pool, while 6 enriched cDNA clones (UH-RA.12-UH-RA.17) were identified from the selections on the RF− ACPA− RA pool. Remarkably, 5 common phage clones (UH-RA.18-UH-RA.22) were attained from selections on both pools. Eighteen out of these 22 identified phage clones were enriched in the fourth selection round. They were almost always detected in earlier selection rounds as well, albeit in decreasing frequencies, indicating enrichment of these phage clones with increasing rounds of selection. The other 4 phage clones were detected multiple times in earlier selection rounds: phage clones UH-RA.9, UH-RA.15 and UH-RA.16 were enriched in the third selection round, while clone UH-RA.11 was found 2 times in the second selection round.

4. Phage ELISA Screening of 22 Enriched Candidate Clones with Sera Used for Affinity Selections To confirm that enrichment of the 22 candidate clones had occurred based on interactions with RA patient antibodies, immunoreactivities against the phage clones were analysed in the individual RA sera that made up the pools by means of a phage ELISA technique. Phage displaying a specific cDNA product were incubated with individual serum specimens, and if individual serum contained antibodies directed against the phage displayed cDNA product, formation of phage-antibody complexes occurred, followed by detection of these complexes.

An excellent association was demonstrated between the selected cDNA clones and immunoreactivity of the individual sera from the pools towards the clones; immunoreactivity against all 22 clones (100%) was found in at least 1 out of 10 serum samples from the corresponding pool, confirming enrichment based on humoral immunoreactivity towards the clones. For sixteen out of 20 sera (80%) from both pools, immunoreactivity was shown towards at least one of the 22 clones.

5. Serological Analysis of the 22 Enriched Clones

To determine which enriched phage clones were characterised by RA-related immunogenicity, phage ELISA was performed on all 22 clones using 38 RA samples that were not used for affinity selections, 38 healthy control sera and 30 sera from patients with other rheumatic inflammatory diseases (table 1) to analyse the frequency of antibody responses. Results are shown in table 5.

For 14 out of 22 enriched clones no reactivity in the 38 HC samples was found, constituting clones with a RA-related serological profile. For the remaining 8 enriched phage clones however, reactivity was also detected in the HC group (table 5). Moreover, antibodies against 11 out of the 14 RA-related clones are specifically detected in RA patients, while for the remaining 3 (UH-RA.1, UH-RA.13 and UH-RA.21) immunoreactivities were also shown in the patient group of other rheumatic diseases.

Immunoreactivity towards UH-RA.21 was detected in approximately one third of our RA study population: 15 out of 48 RA patients (31%) had elevated antibody levels against this clone. However, also 6 out of 30 rheumatic control patient samples showed reactivity to the cDNA clone: 4 out of 6 being sera from ankylosing spondylitis patients, the other 2 sera from psoriatic arthritis patients. Immunoreactivity towards UH-RA.1 could be detected in 6 out of 48 RA patients (13%), but also in 2 out of 19 ankylosing spondylitis patients.

Clones UH-RA.9, UH-RA.10, UH-RA.11, UH-RA.14, UH-RA.15 and UH-RA.16 on the other hand, also showed a relatively high frequency of immunogenicity in RA patients as shown in table 5. Moreover, this immunogenicity is RA-specific and was not detected in the rheumatic control group. For 8 out of 48 RA patients (17%) elevated antibody levels against UH-RA.14 were found. Humoral immunoreactivity towards UH-RA.9, UH-RA.10, UH-RA.11, UH-RA.15 and UH-RA.16 was demonstrated in respectively 4 (8%), 5 (10%), 6 (13%), 4 (8%) and 3 (6%) out of 48 RA patients.

6. Sequence Analysis

Sequence analysis of the 14 clones with RA-related serological profile was performed to obtain the identity of the RA-related antigenic panel. Nucleotide and amino acid sequences were compared to GenBank and Swissprot databases with NCBI BLAST homology search. Nucleotide and amino acid sequences of the 14 clones are shown in table 6 and 7 respectively.

At the nucleotide level, we could find 100% homology with database (c)DNA sequences for all identified 14 cDNA clones. The length of the corresponding displayed peptides varied between 5 and 176 amino acids.

Four out of the 14 cDNA clones (UH-RA.11, UH-RA.15, UH-RA.16 and UH-RA.17) encoded (parts of) known proteins: MHC class I A, mitotin, ribosomal protein S6 and selenoprotein P (SEPP1). All other clones constitute novel peptide sequences resulting from expression of novel cDNA sequences, out of frame expression of known cDNAs or expression of untranslated mRNA regions (for example 3'UTR regions). For these novel peptides we could not find 100% homology with known proteins by performing BLAST in the Swissprot database. However, we detected partial homologies to known proteins at amino acid level as shown in table 7.

7. Association Between RA and Immunoreactivity Towards Antigenic Panel

For the identified panel of 14 clones, a sensitivity of 58% in our RA study population was attained: elevated antibody levels against at least one clone from the panel were detected in 28 out of 48 RA patients. However, immunoreactivity against our panel was also demonstrated in 10 out of 68 tested controls (10 out of 30 patients with other rheumatic diseases), constituting a specificity for RA of 85%. However, all 28 RA patients for whom immunoreactivity was shown towards our panel of 14 clones, were also detected by reactivity towards only 6 clones (UH-RA.1, UH-RA.9, UH-RA.10, UH-RA.11, UH-RA.14 and UH-RA.21) out of this panel. For this panel of 6 clones, specificity was increased to 91%, while maintaining equal sensitivity: for only 7 out of 30 rheumatic control patients immunoreactivity was found towards at least one of the 6 phage clones. Analysing reactivities towards our panel of 14 clones in another RA study group however, could lead to increasing sensitivities compared to an antigenic panel comprising only 6 clones. Moreover, antibodies against 11 out of the 14 RA-related clones were specifically detected in RA patients while for the remaining 3 clones (UH-RA.1, UH-RA.13 and UH-RA.21) reactivity was also found in the patients with other rheumatic diseases. For these 11 RA-specific clones, a sensitivity of 44% and specificity of 100% was obtained.

Next, a possible association between diagnosis of RA and antibody positivity towards clones from our panel was analysed. A very significant association between diagnosis of RA and immunoreactivity against at least one of the antigenic panel of 14 cDNA products (Fisher's exact test: p<0.001) was detected. In addition, a statistically significant association between diagnosis of RA and antibody positivity against UH-RA.9, UH-RA.11, UH-RA.10, UH-RA.14, UH-RA.15 and UH-RA.21 clones separately was found (p<0.05).

Furthermore, levels of antibody reactivity towards a particular cDNA clone were compared between the different study populations, namely RA patients, patients with other rheumatic diseases and healthy controls by Kruskall-Wallis testing. When comparing our RA study group with the healthy control group, statistically significant differences in antibody levels were detected for 7 of the 14 RA-associated clones (UH-RA.9, UH-RA.10, UH-RA.13, UH-RA.14, UH-RA.17, UH-RA.21 and UH-RA.22). Moreover, for UH-RA.10, UH-RA.14 and UH-RA.21, significantly different antibody levels were found when comparing the RA group with the other rheumatic diseases patient group. The levels of antibody reactivity towards UH-RA.10 and UH-RA.21 in the different study populations are shown in FIG. 2.

8. Association Between RF and ACPA Serology and Immunoreactivity Towards Antigenic Panel We examined whether the presence of antibodies against at least one of the 14 clones from the panel was associated with a particular RF and ACPA serological profile. After subdividing our RA study population according to RF and ACPA serology, immunoreactivity against at least one of the 14 clones was detected in 3 out of 5 (60%) RF+ ACPA−, 11 out of 17 (65%) RF+ ACPA+, 12 out of 22 (55%) RF− ACPA− and 2 out of 4 (50%) RF− ACPA+ RA patients. No statistically significant association between antibody reactivity towards the panel and RF and ACPA serological profile could be demonstrated.

Screening for Antibody Reactivity towards the Identified Antigenic Panel is of Added Value to ACPA and RF Serological Testing.

Thirty-one out of 48 RA patients (65%) from our initial RA study population were seronegative for at least one of the 2 diagnostic RA markers, RF and ACPA. Moreover, 22 out of these 31 (46% of the initial RA study population) were serologically negative for both. Based on standard diagnostic laboratory testing for RA, half of our RA study patients thus constituted a diagnostic "difficulty". Since sampling of RA patients was done randomly, this high percentage of seronegative patients clearly underscores the need for additional RA markers. By detecting antibodies against at least one of our 14 identified cDNA products, we were able to identify 17 out of 31 (55%) RA patients that were seronegative for at least one of the 2 standard diagnostic markers: immunoreactivity against our panel was detected in 12/22 (55%) RF− ACPA−, 3/5 (60%) RF+ ACPA− and 2/4 (50%) RF− ACPA+ RA patients. The measurement of RF and/or ACPA enabled the identification of 54% of RA patients from the initial study group, and by adding the detection of antibodies against one of the 11 RA-specific clones to the diagnostic test, serological sensitivity was increased to 71% (17% increase). Moreover, if antibody-detection against one of the 3 RA-associated clones was included, a sensitivity of 79% was attained (25% increase).

Moreover, a search was performed for a possible association between the presence of antibodies against a particular individual clone from the panel and a RF and ACPA serological profile. An association between humoral immunoreactivity towards particular cDNA clones and RF and ACPA negative serology was found. The RA patients in our study population that showed reactivity towards UH-RA.2, UH-RA.15 and UH-RA.16 (1, 4 and 3 RA patients respectively), were all found to be serologically negative for RF and ACPA demonstrating a specific immunogenicity in RF− ACPA− RA patients of these 3 clones. Also, 5 out of 6 RA patients immunoreactive against UH-RA.11, were RF and ACPA negative. For the UH-RA.14 clone 7 out of 8 positive RA patients were shown to be ACPA negative (5 patients are RF− and 2 are RF+). However, these associations of antibody-positivity towards particular clones and a seronegative RA phenotype were not statistically significant, probably due to low patient numbers.

9. Autoantibody Reactivity and Demographic and Clinical Data

We examined and compared demographic and disease variables between RA patients positive for at least one of the 14 RA-associated clones and RA patients who were considered antibody-negative for this panel. We compared age, gender, age of disease onset, disease duration, levels of C-reactive protein (CRP) and erythrocyte sedimentation rates (ESR) (both at sampling and at 3-year follow-up), active versus inactive disease phase and erosive versus non-erosive disease between the antibody-positive and negative RA populations.

No differences were observed in age, gender, age of disease onset, active versus inactive disease phase and erosive versus non-erosive disease. We could however identify a significant association (p=0.0087) between antibody-positivity towards at least one of the 14 clones and early disease duration in our RA study population, as shown in FIG. 3. This could possibly in part be explained by the fact that affinity selections were performed with an early disease RA subgroup, leading to preferential selection of antigen targets associated with an early disease phase. Furthermore, we detected a statistically significant association between antibody-positivity towards our panel and higher CRP levels at sampling and at follow-up (p=0.0146 and p=0.032 respectively) compared to the antibody-negative RA subpopulation. Humoral reactivity towards our antigenic panel is thus associated with higher levels of inflammation at sampling and is predictive for higher inflammatory disease activity at follow-up. In addition, to examine whether reactivity against an individual clone from the panel was associated with a particular RA phenotype, we compared the same demographic and disease variables in the RA patients who were antibody-positive for this particular clone and antibody-negative patients. On individual clone level there were no significant differences in age, gender, age of disease onset, active versus inactive disease phase and erosive versus non-erosive disease. For clones UH-RA.10, UH-RA.14 and UH-RA.15 however, an association between antibody-positivity and shorter disease duration was detected (p<0.001). Regarding CRP levels, two different trends could be discerned. Positivity for UH-RA.11 or UH-RA.14 was significantly associated with decreased CRP levels at follow-up (p<0.05). This could partly be explained by the preferential reactivity towards these two clones in RF− and/or ACPA− RA patients, since this phenotype is associated with a positive prognosis (12). Positivity for UH-RA.21 on the other hand is associated with higher CRP levels at sampling (p<0.01).

The level of antibody reactivity towards all individual clones was investigated for correlation to disease duration, age, age of disease onset, CRP and ESR levels (both at sampling and at follow-up) (Spearman correlation). For UH-RA.11, UH-RA.14, UH-RA.15 and UH-RA.17, a negative correlation between antibody levels and disease duration was demonstrated ($r_s=-0.43$, $r_s=-0.34$, $r_s=-0.39$, $r_s=-0.42$ respectively). Reactivity towards these clones is thus associated with an early disease course.

10. Serological Analysis of the 14 RA-Associated and RA-Specific Clones

Antibody levels against the 14 identified clones measured with phage ELISA screening in all RA and control serum samples are depicted in FIG. 4 (UH-RA.9, UH-RA.10, UH-RA.13, UH-RA.14, UH-RA.17, UH-RA.21 and UH-RA.22) and in FIG. 5 (UH-RA.1, UH-RA.2, UH-RA.7, UH-RA.11, UH-RA.15, UH-RA.16 and UH-RA.20).

11. Confirmation of Sensitivity of the 14 Clone Panel in an Independent RA Validation Cohort To further validate our candidate panel of 14 clones, we analysed the immunoreactivities towards our panel in another, independent RA cohort comprising 44 RA patients. Results obtained from phage ELISA screening with the 44 additional sera on the 14 clones from the panel are shown in table 8. In total, 21 out of 44 tested RA patients tested positive for the presence of antibodies towards our panel, comprising a sensitivity of the panel in this patient group of 48%. This is in line with the sensitivity obtained in the first RA test population. By combining the results obtained for the RA validation cohort with those from the RA study cohort, a sensitivity of the panel for RA of 53% (49 out of 92 RA patients) is attained. Also, antibodies against UH-RA.21 were detected in 11 out of 44 patients (25%) of this RA test group, confirming the relevance of this antigen-antibody system. For most candidate clones, the immunoreactivity percentages obtained by screening the RA validation cohort are comparable with those from the first study population. However, a trend for higher sensitivity levels in the initial RA study population was discerned, which can be explained by the fact that this population also comprised the patients that were used for the actual affinity selection procedures.

12. Expression of Candidate Antigens in RA Synovial Tissue

For 3 identified candidate antigens, HLA-A (UH-RA.11), ribosomal protein S6 (UH-RA.16) and MCM2 (UH-RA.15), monoclonal or polyclonal antibodies could be commercially obtained. Staining with these antibodies was performed on synovial knee tissue from three RA patients, all characterised by severe joint destruction. As a negative control, synovial knee tissue from a patient with destructive gonarthrosis was used. For all three proteins, staining was detected in the synovial tissues from all 3 RA patients, in comparison to the absence of detectable staining in the rheumatic control sample (not shown). This complies with elevated expression of these proteins in inflamed RA tissue. For HLA-A and ribosomal protein S6, staining seemed to be associated with inflammatory infiltrates, while this could not be observed for MCM2.

As for UH-RA.21 no antibody or antiserum could be commercially obtained, human anti-UH-RA.21 antibodies were immuno-affinity purified from a positive RA serum sample by the use of UH-RA.21 coated beads. Immunohistochemical staining with the polyclonal anti-UH-RA.21 antiserum on the synovial tissue from 3 RA patients and 1 control rheumatic patient was performed, resulting in a positive staining in one RA synovial tissue. In this tissue, staining was demonstrated to be predominantly located at inflammatory infiltrates and in the hyperproliferating synovial lining (not shown).

13. Further Characterization of UH-RA.21 by Peptide ELISA Screening

By application of a synthetic peptide ELISA procedure, more serum samples from RA patients and different control groups were screened for anti-UH-RA.21 immunoreactivity. Peptide ELISA screening was performed on sera from 78 RA patients, 48 healthy control subjects (HC), 42 subjects with mechanical joint complaints, 49 osteoarthritis (OA) patients, 26 psoriatic arthritis patients and 35 ankylosing spondylitis patients. Background reactivity was accounted for by measuring immunoreactivity towards a non-relevant peptide. The cut-off value for a positive signal was 3× SD above the mean of the HC and mechanical joint complaints group combined, with exclusion of outliers. In FIG. 7, the results of the peptide ELISA screening are depicted. Eighteen out of 78 RA patients (23%), 6 out of 49 OA patients (12%), 5 out of 26 psoriatic arthritis patients (19%), 5 out of 35 ankylosing spondylitis patients (14%), 2 out of 48 HC (4%) and 1 out of 42 subjects with mechanical joint complaints (2%) were antibody-positive for UH-RA.21. Significant differences in antibody-reactivity towards UH-RA.21 were demonstrated between RA patients and the combined group of HC and mechanical joint complaints subjects on the one hand, and between RA patients and OA patients on the other.

Materials and Methods

1. Construction of a RA cDNA Phage Display Library

Synovial tissue, obtained at total hip replacement surgery of a 64-year old male patient with a 20-year history of seropositive RA, was used for RA library construction. The synovial tissue was analysed immunohistochemically by staining for the presence of inflammatory cells such as macrophages (CD68+), T-cells (CD3+) and B-cells (CD20+). Poly(A)+ RNA was directly isolated (polyATtract system 1000, Promega, Leiden, the Netherlands) from the synovial tissue without prior total RNA isolation as described by the manufacturer. Oligo(dT) linker-primed cDNA was cloned into a λ-Uni-ZAP XR vector system (Stratagene, La Jolla, USA) followed by packaging of λ phage. After mass excision of the pBluescript SK(−) phagemid from the Uni-ZAP XR vector, cDNA inserts were obtained by XhoI-XbaI (New England Biolabs, Ipswich, USA) restriction digestion. cDNA inserts (sizes 500-2500 bp) were gel-purified (GFX gel band purification kit, GE Healthcare, Diegem, Belgium) and subsequently directionally cloned into our XhoI-XbaI digested pSPVI-A/B/C phagemid vectors, each encoding a different reading frame. cDNA cloning occurs via C-terminal fusion to the pVI phage minor coat protein, resulting in display of the encoded cDNA products at the phage surface (21;22). After transformation of ligation mixtures into electrocompetent TG1 *E. coli* bacteria (Stratagene), RA-pSPVI-A/B/C display libraries were obtained. Sequencing was performed on each phage display library.

2. RA Patients and Controls

Serum samples were obtained from 48 RA patients, who were diagnosed based on fulfilment of the ACR criteria. Patient characteristics are summarized in table 1.

Determination of RF serology was performed with the Serodia-RA Particle Agglutination test (Fujirebio Diagnostics, Goteberg, Sweden) according to the manufacturer's instructions. ACPA measurements were performed with a second-generation (anti-CCP2) ELISA test (Quanta Lite CCP IgG, INOVA Diagnostics, San Diego, USA), with a cut off value of 20 IU to define a positive test.

For affinity selections, two serum pools from 10 RA patients each were used. Characteristics of patients used for affinity selections are shown in table 2 and 3. The first pool consisted of sera from randomly selected RA patients with early disease course (symptoms of less than 1 year) (table 2). In this early RA patient group, 4 patients were serologically negative for RF and ACPA (RF− ACPA−), 2 were positive for both markers (RF+ ACPA+), while the remaining four were positive for just one of the two markers (2 patients were RF+ ACPA− and 2 were RF− ACPA+). The second pool contained sera from RF− ACPA− RA patients (table 3).

Both serum pools were, prior to use in SAS, depleted of antibodies against bacterial and phage components as previously described (23;24) and subsequently stored in aliquots at −80° C.

To perform detailed serological analysis by phage ELISA screening for clones identified by SAS, serum samples of 38 healthy controls (HC) and 30 patients with other inflammatory rheumatic diseases (19 ankylosing spondylitis, 8 psoriatic arthritis and 3 Sjögren's syndrome patients) were obtained (Table 1). All sera used in phage ELISA screening showed equivalent total serum IgG levels. After collection, serum samples were aliquoted and stored at −80° C.

3. Serological Antigen Selection of a RA cDNA Phage Display Library

The Serological Antigen Selection procedure was applied on the RA cDNA phage display library as described (24;25). Four subsequent affinity selection rounds were performed in parallel with the early and RF− ACPA− RA serum pools. To enrich for phage clones based on high-affinity interactions with RA patient immunoglobulins (IgG), the selection procedure was performed more stringent with increasing rounds of selection.

4. Screening for Enriched cDNA Clones

Identification of enriched cDNA clones was performed by colony PCR followed by restriction enzyme digestion as described in (24;25) with minor modifications. Primers used for PCR were forward primer (5'-TTA CCC TCT GAC TTT GTT CA-3' (SEQ ID NO:29)) and reverse primer (5'-CGC CAG GGT TTT CCC AGT CAC GAC-3' (SEQ ID NO:30)) (Eurogentec, Ougree, Belgium), which annealed to the phagemid vector at either end of the cDNA insert.

5. Sequence Analysis

Sequencing was performed on purified PCR products (GFX PCR DNA purification kit, GE Healthcare) of individual clones with primer 5'-TTA CCC TCT GAC TTT GTT CA-3' (SEQ ID NO:29) (Eurogentec), which annealed to the phagemid gene encoding pVI, and Big Dye TMT Terminator Cycle Sequence Ready Reaction Kit II (Applied Biosystems, Warrington, United Kingdom), followed by analysis on an ABI Prism 310 Genetic Analyser (Applied Biosystems). Homology search analysis of nucleotide and amino acid sequences was performed with the basic local alignment search tool software of NCBI.

6. Phage ELISA

The level of antibody reactivity of individual serum samples against individual selected phage clones was measured by phage ELISA. ELISA of ligand displaying phage was performed as described previously (23;24). Background reactivity against phage particles was accounted for by measuring the ELISA signal obtained by incubating the tested serum sample with empty phage, in parallel to incubation with the tested phage clone encoding a specific cDNA product. A serum sample with an OD(tested phage):OD (empty phage) ratio higher than 3 times the standard deviation (SD) above the mean ratio OD(tested phage):OD(empty phage) of the HC group, was considered positive for antibodies against the encoded cDNA product. Experiments were performed independently in duplicate or triplicate. Results were expressed as mean ratio OD(tested phage):OD (empty phage).

7. Statistical Analysis

Statistical analysis was performed using GraphPad Prism version 4.0. A p-value of <0.05 was considered statistically significant. The levels of antibody reactivity as measured by mean phage ELISA ratios in RA patients and control groups were compared using Kruskall-Wallis testing. Quantitative demographic variables for antibody-positive and antibody-negative patients were compared using student t-tests and categorical variables were compared by Fisher's exact test. Associations between positivity for antibodies against particular cDNA clones and diagnosis of RA, were analysed by Fisher's exact test. Correlations between antibody levels and different clinical variables were examined by Spearman's correlation coefficient.

8. Recombinant Protein Expression and Purification

Recombinant protein expression is performed according to the pBAD/TOPOThioFusion kit (Invitrogen, Merelbeke, Belgium). The recombinant protein is expressed as a fusion protein to thioredoxin at the N-terminal side and a His6-tag at the C-term. The cDNA insert encoding the candidate antigen was amplified and PCR products were cloned into the pBAD/TOPOThioFusion vector followed by transformation of the ligation mixtures into TOP10 *E. coli* bacteria. For protein expression, plasmids were isolated and transformed into LMG194 *E. coli* bacteria. LMG194 bacteria, containing the pBAD/TOPO vector with insert, were cultured in LB medium (Invitrogen) to OD600 of 0.5 after which recombinant protein expression was induced during 4 hours by arabinose (0.2%) addition. After centrifugation, bacterial cells were resuspended in lysis buffer (6M guanidiumchloride, 20 mM sodium phosphate, 500 mM NaCl, pH 7.8) followed by sonication for disruption of protein inclusion bodies. Recombinant protein purification was performed with Ni-NTA Sepharose beads (IBA, Leusden, the Netherlands) followed by dialysis against PBS. Protein identity was confirmed by performing SDS-PAGE followed by excision of the protein band and ESI-LC-MS/MS analysis (ThermoFinnigan, San Jose, US). The purified protein concentration was determined with the BCA protein quantification kit (Fisher Scientific, Doornik, Belgium).

9. Peptide/Protein ELISA and Competition ELISA

Synthetic purified peptides (Eurogentec) were coated at 1 µg/ml in PBS (pH 7.4) overnight at room temperature in peptide ELISA plates (polystyrene flat-bottom ELISA plates, Greiner Bio-One, Wemmel, Belgium). Recombinant proteins were coated at 1 µg/ml in carbonate buffer (0.1 M sodium hydrogen carbonate, pH 9.6) overnight at 4° C. in ELISA plates (Greiner Bio-One). After washing with 0.05% PBS-Tween20 (PBS-T), blocking was performed with 2% milk powder in PBS (M-PBS) for 2 hours at 37° C. After washing, serum samples were incubated (1/100 diluted in M-PBS) with the coated ELISA plates for 2 hours at room temperature. Following washing, detection of antibody binding was performed by incubation with rabbit anti-human IgG HRP-antibody (1/1500 in M-PBS) (DAKO, Heverlee, Belgium) followed by colour development with TMB substrate (3,3',5,5'tetramethylbenzidine) (Sigma-Aldrich, Bornem, Belgium). The reaction was stopped by addition of 2M H2SO4 and colour development was read at 450 nm. As negative controls, a non-relevant peptide and a thioredoxin protein synthesised in an identical manner were used at identical concentrations. For peptide ELISA, a ratio of OD(tested peptide)/OD(non-relevant peptide) of more than 1.5 was considered a positive signal. For protein ELISA, a ratio of OD(protein)/OD(thioredoxin) of more than 1.5 was used as cut-off for a positive signal. Samples were tested in duplicate within a single experiment, and experiments were performed in duplicate.

To further confirm specificity of measured antibodies towards phage displayed cDNA products, a competition ELISA between purified peptide and phage displaying the corresponding peptide was applied. Before incubation of the 1/100 diluted serum samples with peptide coated wells, the serum samples were pre-incubated with increasing amounts of phage displaying the peptide at the surface. Competition of phage-displayed peptide with the coated peptide for serum antibodies results in decreased OD signals. As a negative control, increasing amounts of empty phage were pre-incubated with the serum samples.

10. Immunohistochemical Analysis of Synovial Tissue

Formalin-fixed, paraffin-embedded tissue sections from RA and control synovial tissue were stained with anti-CD3 (Klinipath, Olen, Belgium), anti-CD68 (Abcam, Heidelberg, Germany) and anti-CD20 antibody (Dako), diluted according to manufacturer's recommendations. Staining synovial tissue for candidate RA target antigens was performed with rabbit polyclonal anti-HLA-A antibody (1/1000) (Abnova, Boechout, Belgium), rabbit polyclonal anti-mitotin antibody (Abnova) (1/1000) and a monoclonal mouse anti-ribosomal protein S6 antibody (1/50) (Abcam). Immuno-affinity purified anti-UH-RA.21 antiserum was diluted 1/50 for immunostainings.

Paraffin-embedded sections were mounted on polysine-coated glass slides (VWR, Heverlee, Belgium) and after dewaxing and rehydrating, endogenous peroxidase activity was blocked by incubation of the slides in a 0.3% hydrogen peroxide in methanol solution during 10 minutes. For the commercially obtained antibodies prevention of a specific binding was performed by incubation of the sections with protein block (Dako) during 20 minutes at room temperature. Primary antibody incubation (in TBS) was performed overnight at room temperature, followed by incubation with a biotin-conjugated secondary antibody (polyclonal swine anti-rabbit Ig antibody 1/300 in TBS or polyclonal rabbit anti-mouse Ig antibody 1/200 in TBS) (Dako) during 1 hour at room temperature. After application of the ABC kit (Dako), staining was performed with DAB (3,3'diaminobenzidine) substrate (Sigma-Aldrich). As the use of a primary human antibody on human tissue gives rise to high background binding, the synovial tissue sections were blocked with non-conjugated secondary antibody, namely rabbit anti-human IgG polyclonal antibody (Dako) diluted 1/100 in TBS supplemented with 10% rabbit serum (Chemicon, Heule, Belgium) during 1 hour at room temperature. Anti-RA.21 antiserum was diluted 1/50 in TBS and incubated overnight at room temperature, followed by 1 hour incubation at room temperature with HRP-conjugated rabbit anti-human IgG antibody (Dako) diluted 1/80 in TBS. Staining was performed with DAB substrate.

TBS and TBS supplemented with 0.05% TritonX-100 were used for in between washing steps. Counterstaining was performed with Gill's haematoxylin (Klinipath). Control staining for each antibody was performed by omitting the primary antibody.

11. Immuno-Affinity Purification of Anti-UH-RA.21 Antibodies Out of RA Serum

Synthetic UH-RA.21 peptide was coupled to AminoLink columns of beaded agarose (MicroLink Protein Coupling Kit, Fisher Scientific) according to the manufacturer's instructions. In short, 100 µg UH-RA.21 synthetic peptide was covalently coupled to AminoLink Plus Coupling Gel Spin Column by incubation in coupling buffer (0.1 M sodium phosphate, 0.15 NaCl, pH 7.2) with addition of sodium cyanoborohydride solution (5M, in 0.01 M NaOH) during 4 hours at room temperature. After blocking of the remaining active sites by washing with quenching buffer (1 M Tris-HCl, 0.05% NaN3, pH 7.4), the UH-RA.21 coupled column was incubated 4 times with 250 µl RA serum containing high antibody levels against UH-RA.21 (according to phage ELISA and peptide ELISA). After washing the column with 0.5M NaCl, the bound antibodies were eluted in three fractions with 100 µl ImmunoPure elution buffer (pH 2.8). Eluates were immediately neutralised by addition of 5 µl of 1M Tris (pH 9.0). Eluates and flow-throughs were evaluated for anti-UH-RA.21 antibody levels by peptide ELISA. The concentration of eluted antibody was determined by spectrophotometry and the BCA protein quantification kit.

Tables

TABLE 1

Characteristics of the study population

| Diagnosis | Number | Gender (Female/Male) | Mean age (SD) (range) in years |
|---|---|---|---|
| RA | 48 | 33/15 | 57.0 (11.3) (34-80) |
| RF− ACPA+ | 4 | 3/1 | 58.5 (9.3) (50-68) |
| RF− ACPA− | 22 | 18/4 | 57.1 (12.2) (37-80) |
| RF+ ACPA+ | 17 | 9/8 | 57.1 (11.8) (34-73) |
| RF+ ACPA− | 5 | 3/2 | 54.7 (7.1) (45-63) |
| Rheumatic controls | 30 | 14/16 | 45.9 (10.1) (33-65) |
| Ankylosing spondylitis | 19 | 6/13 | 42.7 (9.9) (33-63) |
| Psoriatic Arthritis | 8 | 5/3 | 53.5 (8.1) (43-65) |
| Sjögren's syndrome | 3 | 3/0 | 44.7 (4.9) (39-48) |
| Healthy controls | 38 | 23/15 | 48.8 (18.4) (24-83) |

TABLE 2

Characteristics of patients with early disease course (early RA serum pool) used for affinity selections

| Subject | Gender[a] | RF status | ACPA status | Age | Disease duration[b] |
|---|---|---|---|---|---|
| RA-p1.1 | F | + | + | 55 | 10 |
| RA-p1.2 | F | + | − | 54 | 12 |
| RA-p1.3 | F | − | + | 68 | 7 |
| RA-p1.4 | M | − | − | 80 | 9 |
| RA-p1.5 | F | − | + | 50 | 3 |
| RA-p1.6 | F | + | − | 63 | 12 |
| RA-p1.7 | F | − | − | 49 | 9 |
| RA-p1.8 | F | − | − | 59 | 12 |
| RA-p1.9 | M | + | + | 46 | 8 |
| RA-p1.10 | F | − | − | 58 | 5 |

[a] F (female) and M (male)
[b] in months after start of symptoms

TABLE 3

Characteristics of RF− ACPA− patients used for RF− ACPA− serum pool affinity selections

| Subject | Gender[a] | RF status | ACPA status | Age | Disease duration[b] |
|---|---|---|---|---|---|
| RA-p2.1 | M | − | − | 41 | 13 |
| RA-p2.2 | F | − | − | 52 | 13 |
| RA-p2.3 | F | − | − | 57 | 14 |
| RA-p2.4 | F | − | − | 69 | 14 |
| RA-p2.5 | M | − | − | 37 | 16 |
| RA-p2.6 | F | − | − | 73 | 5 |
| RA-p2.7 | F | − | − | 65 | 7 |
| RA-p2.8 | F | − | − | 68 | 14 |
| RA-p2.9 | F | − | − | 66 | 4 |
| RA-p2.10 | F | − | − | 37 | 3 |

[a] F (female) and M (male)
[b] in years

TABLE 4

Serological Antigen Selection procedure for the early and RF− ACPA− RA pools: increase in phage output:input titers with increasing selection round

| Round | Output:Input ratio | |
|---|---|---|
| | Early RA pool | RF− ACPA− RA pool |
| 1 | $3.7 \times 10^{-8}$ | $2.6 \times 10^{-8}$ |
| 2 | $1.1 \times 10^{-8}$ | $1.5 \times 10^{-8}$ |
| 3 | $1.0 \times 10^{-7}$ | $5.0 \times 10^{-8}$ |
| 4 | $3.7 \times 10^{-7}$ | $3.4 \times 10^{-7}$ |

TABLE 5

ELISA screening for the panel of 22 candidate phage cDNA clones

| Clone | RA | Rheumatic controls | Healthy controls |
|---|---|---|---|
| Clones with RA-related serological profile | | | |
| UH-RA.1 | 6/48 (13%) | 2/30 (7%) | 0/38 (0%) |
| UH-RA.2 | 1/48 (2%) | 0/30 (0%) | 0/38 (0%) |
| UH-RA.7 | 1/48 (2%) | 0/30 (0%) | 0/38 (0%) |
| UH-RA.9 | 4/48 (8%) | 0/30 (0%) | 0/38 (0%) |
| UH-RA.10 | 5/48 (10%) | 0/30 (0%) | 0/38 (0%) |
| UH-RA.11 | 6/48 (13%) | 0/30 (0%) | 0/38 (0%) |
| UH-RA.13 | 2/48 (4%) | 3/30 (10%) | 0/38 (0%) |
| UH-RA.14 | 8/48 (17%) | 0/30 (0%) | 0/38 (0%) |
| UH-RA.15 | 4/48 (8%) | 0/30 (0%) | 0/38 (0%) |
| UH-RA.16 | 3/48 (6%) | 0/30 (0%) | 0/38 (0%) |
| UH-RA.17 | 1/48 (2%) | 0/30 (0%) | 0/38 (0%) |
| UH-RA.20 | 1/48 (2%) | 0/30 (0%) | 0/38 (0%) |
| UH-RA.21 | 15/48 (31%) | 6/30 (20%) | 0/38 (0%) |
| UH-RA.22 | 2/48 (4%) | 0/30 (0%) | 0/38 (0%) |
| Total | 28/48 (58%) | 10/30 (33%) | 0/38 (0%) |
| Clones with non-RA-related serological profile | | | |
| UH-RA.3 | 3/48 (6%) | 2/30 (7%) | 1/38 (3%) |
| UH-RA.4 | 2/48 (4%) | 0/30 (0%) | 1/38 (3%) |
| UH-RA.5 | 3/48 (6%) | 0/30 (0%) | 4/38 (11%) |
| UH-RA.6 | 5/48 (10%) | 1/30 (3%) | 2/38 (5%) |
| UH-RA.8 | 2/48 (4%) | 4/30 (13%) | 4/38 (11%) |
| UH-RA.12 | 3/48 (6%) | 0/30 (0%) | 3/38 (8%) |
| UH-RA.18 | 6/48 (13%) | 1/30 (3%) | 1/38 (3%) |
| UH-RA.19 | 3/48 (6%) | 5/30 (17%) | 2/38 (5%) |
| Total | 34/48 (71%) | 15/30 (50%) | 15/38 (39%) |

TABLE 6

Sequence analysis of 14 RA-associated cDNA clones

| Clone | cDNA identity | NCBI number | coding sequence | in/out of frame |
|---|---|---|---|---|
| UH-RA.1 | HLA class II DQ B1 (B1*050101) | AY663400.1 | 3'UTR | |
| UH-RA.2 | Homo sapiens fat mass and obesity associated (FTO) | BC030798.1 | 3'UTR | |
| UH-RA.7 | Myosin light chain 6 (MYL6) | BC017455.1 | in coding sequence | out of frame |
| UH-RA.9 | Talin 1 | BC042923.1 | 5'UTR + coding sequence | out of frame |
| UH-RA.10 | Chromosome 1 RP11-29H23 clone | AL353807.18 | | |
| UH-RA.11 | MHC class I A | BC019236.2 | in coding sequence | in frame |
| UH-RA.13 | Ribosomal protein L21 | NM_000982.3 | in coding sequence | out of frame |
| UH-RA.14 | Vacuolar protein sorting 24 homolog, plus/minus | NM_016079.2 | | |
| UH-RA.15 | MCM2 minichromosome maintenance deficient 2, mitotin | NM_004526.2 | in coding sequence | in frame |
| UH-RA.16 | 40S ribosomal protein S6 | BC000524.2 | in coding sequence | in frame |
| UH-RA.17 | Selenoprotein P, plasma, 1 (SEPP1) | BC058919.1 | 5'UTR + coding sequence | in frame |
| UH-RA.20 | HLA class II DR beta 1 (HLA-DRB1) | BC024269.1 | in coding sequence | out of frame |
| UH-RA.21 | Bromo adjacent homology domain containing 1 (BAHD1) | NM_014952.3 | 3'UTR | |

TABLE 6-continued

Sequence analysis of 14 RA-associated cDNA clones

| Clone | cDNA identity | NCBI number | coding sequence | in/out of frame |
|---|---|---|---|---|
| UH-RA.22 | Est human eyeball cDNA (similar to ribosomal protein L3) | EL949248.1 | | |

TABLE 7

Peptide identity of 14 RA-associated cDNA clones

| Clone | Translated cDNA product | size (in amino acids) | Homology on amino acid level (Swissprot accession number) |
|---|---|---|---|
| UH-RA.1 | EKRQEITTE* (SEQ ID NO: 6) | 9 aa | 7/9 (77%) T-cell specific transcription factor 1 (P36402)<br>6/7 (85%) transferrin receptor protein 2 (Q9UP52)<br>6/7 (85%) cell division control protein 6 homolog (Q99741) |
| UH-RA.2 | SISTS* (SEQ ID NO: 7) | 5 aa | Multiple hits due to small size of cDNA product<br>5/5 (100%) DnaJ homolog subfamily B member 6 (heat shock protein J2) (O75190)<br>5/5 (100%) dedicator of cytokinesis protein 8 (Q8NF50) |
| UH-RA.7 | SSQDV* (SEQ ID NO: 8) | 5 aa | Multiple hits due to small size of cDNA product<br>5/5 (100%) histone acetyltransferase MYST3 (Q92794)<br>5/5 (100%) macrophage colony stimulating factor precursor (P09603) |
| UH-RA.9 | RSCHHGCTFTEDQHWECG EDDAV* (SEQ ID NO: 9) | 23 aa | 9/14 (64%) Macrophage mannose receptor 2 precursor (Q9UBG0)<br>6/9 (66%) T-cell surface glycoprotein CD1d precursor (CD1d antigen) (P15813)<br>8/13 (61%) Nuclear autoantigen Sp-100 (Speckled 100 kDa) (P23497) |
| UH-RA.10 | SNALENFVYNKFQQNNCV WPGAVAHACNPSTLRG* (SEQ ID NO: 10) | 34 aa | 15/16 (93%) Plakophilin-2 (Q99959)<br><br>14/15 (93%) Alu subfamily (P39190) |
| UH-RA.11 | SSQPTIPIVGIIAGLVLF GAVITGAWAAVMWRRKSS DRKGGSYSQAASSDSAQG SDVSLTACKV* (SEQ ID NO: 2) | 65 aa | 100% (65/65) MHC class I A-2 (P01892)/A-68 (P01891)/A-69 (P10316) |
| UH-RA.13 | QDSCQEN* (SEQ ID NO: 11) | 7 aa | Multiple hits due to small size of cDNA product<br>5/6 (83%) mitotic checkpoint serine/threonine-protein kinase BUB1 (O43683)<br>6/7 (85%) U3 small nucleolar RNA-associated protein 18 homolog (Q9Y5J1)<br>6/10 (60%) C-type lectin domain family 13 member A (Q8IX05) |
| UH-RA.14 | KEELWRQ* (SEQ ID NO: 3) | 7 aa | Multiple hits due to small size of cDNA product<br>6/6 (100%) trichohyalin (Q07283)<br>5/7 (71%) ADAMTS12 (A disintegrin and metalloproteinase with thrombospondin motifs 12) (P58397)<br>6/7 (85%) centrosome and spindle pole-associated protein 1 (Q1MSJ5) |
| UH-RA.15 | DTIEVPEKDLVDKARQIN IHNLSAFYDSELFRMNKF SHDLKRKMILQQF* (SEQ ID NO: 4) | 49 aa | 49/49 (100%) DNA replication licensing factor MCM2 (Minichromosome maintenance protein 2 homolog) (P49736) |
| UH-RA.16 | RLLLSKGHSCYRPRRTGE RKRKSVRGCIVDANLSVL NLVIVKKGEKDIPGLTDT TVPRRLGPKRASRIRKLF NLSKEDDVRQYVVRKPLN | 176 aa | 176/176 (100%) 40S ribosomal protein S6 (Phosphoprotein NP33) (P62753) |

TABLE 7-continued

Peptide identity of 14 RA-associated cDNA clones

| Clone | Translated cDNA product | size (in amino acids) | Homology on amino acid level (Swissprot accession number) |
|---|---|---|---|
| | KEGKKPRTKAPKIQRLVT<br>PRVLQHKRRRIALKKQRT<br>KKNKEEAAEYAKLLAKRM<br>KEAKEKRQEQIAKRRRLS<br>SLRASTSKSESSQK*<br>(SEQ ID NO:5) | | |
| UH-RA.17 | AKRKEAGPLEVVVTTPAM<br>WRSLGLALALCLLPSGGT<br>ESQDQSSLCKQPPAWSIR<br>DQDPMLNSNGSVTW<br>ALLQAS*<br>(SEQ ID NO: 12) | 76 aa | 58/58 (100%) selenoprotein P, precursor, SEPP1 (P49908) |
| UH-RA.20 | RGLHLPSGAPKDEPSHSG<br>MESTV*<br>(SEQ ID NO: 13) | 22 aa | 12/17 (70%) adapter-related protein complex 3 (mu-1 subunit) (Q9Y2T2)<br>11/16 (68%) B-CAM cell surface glycoprotein (P50895)<br>10/15 (66%) TGFbeta 1 induced transcript 1 protein (O43294)<br>8/10 (80%) NF-kappa-B essential modulator (IKKAP1)<br>6/7 (85%) collagen alpha-2 (VIII) chain precursor (P25067)<br>8/12 (66%) calpastatin (calpain inhibitor) (P20810) |
| UH-RA.21 | PGGFRGEFMLGKPDPKPE<br>GKGLGSPYIE*<br>(SEQ ID NO: 1) | 28 aa | 7/7 (100%) B-cell scaffold protein with ankyrin repeats (Q8NDB2)<br><br>7/8 (87%) IL-27 beta chain precursor (Q14213)<br>8/10 (80%) La-related protein 1 (Q6PKG0) |
| UH-RA.22 | FIGRGDKPTEPGDSWLSK<br>IESQFNFKFAHRTL*<br>(SEQ ID NO: 14) | 32 aa | 10/14 (71%) Transcription factor 15 (bHLH-EC2 protein) (Q12870)<br><br>9/19 (47%) Leucine-rich repeat and fibronectin type-III domain containing protein 5 precursor (Q96N16)<br>8/12 (66%) Niban protein (Protein FAM129A) (Cell growth-inhibiting gene 39 protein) (Q9BZQ8) |

TABLE 8

Further validation of RA panel by screening the RA validation cohort

| Clone | RA study cohort | RA validation cohort | Total |
|---|---|---|---|
| UH-RA.1 | 6/48 (13%) | 3/44 (7%) | 9/92 (10%) |
| UH-RA.2 | 1/48 (2%) | 1/44 (2%) | 2/92 (2%) |
| UH-RA.7 | 1/48 (2%) | 1/44 (2%) | 2/92 (2%) |
| UH-RA.9 | 4/48 (8%) | 0/44 (0%) | 4/92 (4%) |
| UH-RA.10 | 5/48 (10%) | 0/44 (0%) | 5/92 (5%) |
| UH-RA.11 | 6/48 (13%) | 6/44 (14%) | 12/92 (13%) |
| UH-RA.13 | 2/48 (4%) | 0/44 (0%) | 2/92 (2%) |
| UH-RA.14 | 8/48 (17%) | 3/44 (7%) | 11/92 (12%) |
| UH-RA.15 | 4/48 (8%) | 1/44 (2%) | 5/92 (5%) |
| UH-RA.16 | 3/48 (6%) | 2/44 (5%) | 5/92 (5%) |
| UH-RA.17 | 1/48 (2%) | 0/44 (0%) | 1/92 (1%) |
| UH-RA.20 | 1/48 (2%) | 0/44 (0%) | 1/92 (1%) |
| UH-RA.21 | 15/48 (31%) | 11/44 (25%) | 26/92 (28%) |
| UH-RA.22 | 2/48 (4%) | 0/44 (0%) | 2/92 (2%) |
| Total | 28/48 (58%) | 21/44 (48%) | 49/92 (53%) |

REFERENCES (1) Gabriel S E. The epidemiology of rheumatoid arthritis. Rheum Dis Clin North Am 2001; 27(2):269-281.

(2) Arnett F C, Edworthy S M, Bloch D A, McShane D J, Fries J F, Cooper N S et al. The American Rheumatism Association 1987 revised criteria for the classification of rheumatoid arthritis. Arthritis Rheum 1988; 31(3):315-324.

(3) Mierau R, Genth E. Diagnosis and prognosis of early rheumatoid arthritis, with special emphasis on laboratory analysis. Clin Chem Lab Med 2006; 44(2):138-143.

(4) Harrison B J, Symmons D P, Barrett E M, Silman A J. The performance of the 1987 ARA classification criteria for rheumatoid arthritis in a population based cohort of patients with early inflammatory polyarthritis. American Rheumatism Association. J Rheumatol 1998; 25(12): 2324-2330.

(5) Huizinga T W, Machold K P, Breedveld F C, Lipsky P E, Smolen J S. Criteria for early rheumatoid arthritis: from Bayes' law revisited to new thoughts on pathogenesis. Arthritis Rheum 2002; 46(5):1155-1159.

(6) Schumacher H R, Pessler F, Chen L X. Diagnosing early rheumatoid arthritis (RA). What are the problems and opportunities? Clinical and Experimental Rheumatology 2003; 21(5):515-519.

(7) O'Dell J R. Treating rheumatoid arthritis early: A window of opportunity? Arthritis and Rheumatism 2002; 46(2):283-285.

(8) Bukhari M, Harrison B, Lunt M, Scott D G I, Symmons D P M, Silman A J. Time to first occurrence of erosions in inflammatory polyarthritis—Results from a prospective community-based study. Arthritis and Rheumatism 2001; 44(6):1248-1253.

(9) Nell V P, Machold K P, Eberl G, Stamm T A, Uffmann M, Smolen J S. Benefit of very early referral and very early therapy with disease-modifying anti-rheumatic drugs in patients with early rheumatoid arthritis. Rheumatology (Oxford) 2004; 43(7):906-914.
(10) Lee D M, Schur P H. Clinical utility of the anti-CCP assay in patients with rheumatic diseases. Ann Rheum Dis 2003; 62(9):870-874.
(11) Nell V P, Machold K P, Stamm T A, Eberl G, Heinzl H, Uffmann M et al. Autoantibody profiling as early diagnostic and prognostic tool for rheumatoid arthritis. Ann Rheum Dis 2005; 64(12):1731-1736.
(12) van der Helm-van Mil A H, Verpoort K N, Breedveld F C, Toes R E, Huizinga T W. Antibodies to citrullinated proteins and differences in clinical progression of rheumatoid arthritis. Arthritis Res Ther 2005; 7(5):R949-R958.
(13) De Rycke L, Peene I, Hoffman I E, Kruithof E, Union A, Meheus L et al. Rheumatoid factor and anticitrullinated protein antibodies in rheumatoid arthritis: diagnostic value, associations with radiological progression rate, and extra-articular manifestations. Ann Rheum Dis 2004; 63(12):1587-1593.
(14) Machold K P, Stamm T A, Nell V P, Pflugbeil S, Aletaha D, Steiner G et al. Very recent onset rheumatoid arthritis: clinical and serological patient characteristics associated with radiographic progression over the first years of disease. Rheumatology (Oxford) 2006.
(15) Rantapaa-Dahlqvist S, de Jong B A, Berglin E, Hallmans G, Wadell G, Stenlund H et al. Antibodies against cyclic citrullinated peptide and IgA rheumatoid factor predict the development of rheumatoid arthritis. Arthritis Rheum 2003; 48(10):2741-2749.
(16) Avouac J, Gossec L, Dougados M. Diagnostic and predictive value of anti-cyclic citrullinated protein antibodies in rheumatoid arthritis: a systematic literature review. Ann Rheum Dis 2006; 65(7):845-851.
(17) Nishimura K, Sugiyama D, Kogata Y, Tsuji G, Nakazawa T, Kawano S et al. Meta-analysis: diagnostic accuracy of anti-cyclic citrullinated peptide antibody and rheumatoid factor for rheumatoid arthritis. Ann Intern Med 2007; 146(11):797-808.
(18) Klareskog L, Stolt P, Lundberg K, Kallberg H, Bengtsson C, Grunewald J et al. A new model for an etiology of rheumatoid arthritis: smoking may trigger HLA-DR (shared epitope)-restricted immune reactions to autoantigens modified by citrullination. Arthritis Rheum 2006; 54(1):38-46.
(19) Irigoyen P, Lee A T, Wener M H, Li W, Kern M, Batliwalla F et al. Regulation of anti-cyclic citrullinated peptide antibodies in rheumatoid arthritis: contrasting effects of HLA-DR3 and the shared epitope alleles. Arthritis Rheum 2005; 52(12):3813-3818.
(20) Verpoort K N, van Gaalen F A, van der Helm-van Mil A H, Schreuder G M, Breedveld F C, Huizinga T W et al. Association of HLA-DR3 with anti-cyclic citrullinated peptide antibody-negative rheumatoid arthritis. Arthritis Rheum 2005; 52(10):3058-3062.
(21) Hufton S E, Moerkerk P T, Meulemans E V, de Bruine A, Arends J W, Hoogenboom H R. Phage display of cDNA repertoires: the pVI display system and its applications for the selection of immunogenic ligands. J Immunol Methods 1999; 231(1-2):39-51.
(22) Jespers L S, Messens J H, De Keyser A, Eeckhout D, Van d B, I, Gansemans Y G et al. Surface expression and ligand-based selection of cDNAs fused to filamentous phage gene VI. Biotechnology (N Y) 1995; 13(4):378-382.
(23) Somers V A, Brandwijk R J, Joosten B, Moerkerk P T, Arends J W, Menheere P et al. A panel of candidate tumor antigens in colorectal cancer revealed by the serological selection of a phage displayed cDNA expression library. J Immunol 2002; 169(5):2772-2780.
(24) Govarts C, Somers K, Hupperts R, Stinissen P, Somers V. Exploring cDNA phage display for autoantibody profiling in the serum of multiple sclerosis patients: optimization of the selection procedure. Ann N Y Acad Sci 2007; 1109:372-384.
(25) Somers V, Govarts C, Hellings N, Hupperts R, Stinissen P. Profiling the autoantibody repertoire by serological antigen selection. J Autoimmun 2005; 25(3):223-228.
(26) Volarevic S, Stewart M J, Ledermann B, Zilberman F, Terracciano L, Montini E et al. Proliferation, but not growth, blocked by conditional deletion of 40S ribosomal protein S6. Science 2000; 288(5473):2045-2047.
(27) Ruvinsky I, Meyuhas O. Ribosomal protein S6 phosphorylation: from protein synthesis to cell size. Trends Biochem Sci 2006; 31(6):342-348.
(28) Tsuruga H, Yabuta N, Hashizume K, Ikeda M, Endo Y, Nojima H. Expression, nuclear localization and interactions of human MCM/P1 proteins. Biochem Biophys Res Commun 1997; 236(1):118-125.
(29) Routsias J G, Tzioufas A G, Moutsopoulos H M. The clinical value of intracellular autoantigens B-cell epitopes in systemic rheumatic diseases. Clin Chim Acta 2004; 340(1-2):1-25.
(30) Hassfeld W, Steiner G, Hartmuth K, Kolarz G, Scherak O, Grainger W et al. Demonstration of a new antinuclear antibody (anti-RA33) that is highly specific for rheumatoid arthritis. Arthritis Rheum 1989; 32(12):1515-1520.
(31) Reichlin M. Cellular dysfunction induced by penetration of autoantibodies into living cells: cellular damage and dysfunction mediated by antibodies to dsDNA and ribosomal P proteins. J Autoimmun 1998; 11(5):557-561.
(32) Marnell L L, Searles R P, Savage S M, Jaramillo Y, Sibbitt W L. Anti-class II beta-chain antibodies in the serum and synovial fluid of rheumatoid arthritis patients. Clin Immunol Immunopathol 1990; 55(2):263-272.
(33) Livneh A, Renert A, Avishai O, Langevitz P, Gazit E. Lymphocytotoxic antibodies in Israeli patients with rheumatoid arthritis. Isr J Med Sci 1997; 33(1):30-35.
(34) Raybourne R B, Bunning V K, Williams K M. Reaction of anti-HLA-B monoclonal antibodies with envelope proteins of *Shigella* species. Evidence for molecular mimicry in the spondyloarthropathies. J Immunol 1988; 140(10):3489-3495.
(35) Naji A, Deschaseaux F, Racadot E, Ferrand C, Justrabo E, Guignier F et al. Induction of tissue factor expression on human umbilical vein endothelial cells by cell-specific HLA class I antibody: preliminary data. Transplant Proc 2005; 37(6):2892-2893.
(36) Burk R F, Hill K E, Motley A K. Selenoprotein metabolism and function: evidence for more than one function for selenoprotein P. J Nutr 2003; 133(5 Suppl 1):1517S-1520S.
(37) Yazar M, Sarban S, Kocyigit A, Isikan U E. Synovial fluid and plasma selenium, copper, zinc, and iron concentrations in patients with rheumatoid arthritis and osteoarthritis. Biol Trace Elem Res 2005; 106(2):123-132.
(38) Canter P H, Wider B, Ernst E. The antioxidant vitamins A, C, E and selenium in the treatment of arthritis: a systematic review of randomized clinical trials. Rheumatology (Oxford) 2007; 46(8):1223-1233.
(39) Pogue-Geile K, Geiser J R, Shu M, Miller C, Wool I G, Meisler A I et al. Ribosomal protein genes are overexpressed in colorectal cancer: isolation of a cDNA clone encoding the human S3 ribosomal protein. Mol Cell Biol 1991; 11(8):3842-3849.
(40) Mincheva A, Todorov I, Werner D, Fink T M, Lichter P. The human gene for nuclear protein BM28 (CDCL1), a new member of the early S-phase family of proteins, maps to chromosome band 3q21. Cytogenet Cell Genet 1994; 65(4):276-277.
(41) Reichlin M. Autoantibodies to the ribosomal P proteins in systemic lupus erythematosus. Clin Exp Med 2006; 6(2):49-52.
(42) Avrameas S, Ternynck T. The Natural Autoantibodies System—Between Hypotheses and Facts. Molecular Immunology 1993; 30(12):1133-1142.
(43) Wang X, Yu J, Sreekumar A, Varambally S, Shen R, Giacherio D et al. Autoantibody signatures in prostate cancer. N Engl J Med 2005; 353(12):1224-1235.
(44) Cepok S, Zhou D, Srivastava R, Nessler S, Stei S, Bussow K et al. Identification of Epstein-Barr virus proteins as putative targets of the immune response in multiple sclerosis. J Clin Invest 2005; 115(5):1352-1360.
(45) Ng B, Yang F, Huston D P, Yan Y, Yang Y, Xiong Z et al. Increased noncanonical splicing of autoantigen transcripts provides the structural basis for expression of untolerized epitopes. J Allergy Clin Immunol 2004; 114 (6):1463-1470.
(46) Olivieri I, van Tubergen A, Salvarani C, van der L S. Seronegative spondyloarthritides. Best Pract Res Clin Rheumatol 2002; 16(5):723-739.
(47) Fitzgerald O, Dougados M. Psoriatic arthritis: one or more diseases? Best Pract Res Clin Rheumatol 2006; 20(3):435-450.

The invention claimed is:

1. An isolated polypeptide comprising SEQ ID NO: 1 or a fragment of SEQ ID NO: 1 containing at least 10 consecutive amino acids of SEQ ID NO: 1, wherein said polypeptide is covalently bound to a solid phase.

2. The isolated polypeptide of claim 1, wherein said solid phase is selected from the group consisting of a microtiter plate, a nylon membrane, a glass bead, a plastic bead, a cellulose support, a silica support, and an agarose support.

3. The isolated polypeptide of claim 1, wherein the polypeptide is recombinantly produced.

4. The isolated polypeptide of claim 1, wherein the polypeptide is attached to a detectable label.

5. The isolated polypeptide of claim 4, wherein said label is selected from the group consisting of an enzymatic label, a chemical label, a fluorescent label, a luminescent label, and a radioactive label.

6. A complex comprising the isolated polypeptide of claim 1 and an autoantibody in a serum sample or a plasma sample of a patient with rheumatoid arthritis.

7. An isolated polypeptide consisting of SEQ ID NO: 1 or a fragment of SEQ ID NO: 1 containing at least 10 consecutive amino acids of SEQ ID NO: 1, wherein said polypeptide is covalently bound to a solid phase.

8. The isolated polypeptide of claim 7, wherein said solid phase is selected from the group consisting of a microtiter plate, a nylon membrane, a glass bead, a plastic bead, a cellulose support, a silica support, and an agarose support.

9. The isolated polypeptide of claim 7, wherein the polypeptide is recombinantly produced.

10. The isolated polypeptide of claim 7, wherein the polypeptide is attached to a detectable label.

11. The isolated polypeptide of claim 10, wherein said label is selected from the group consisting of an enzymatic label, a chemical label, a fluorescent label, a luminescent label, and a radioactive label.

12. A complex comprising the isolated polypeptide of claim 7 and an autoantibody in a serum sample or a plasma sample of a patient with rheumatoid arthritis.

* * * * *

SEQUENCE LISTING

```
<160> NUMBER OF SEQ ID NOS: 30

<210> SEQ ID NO 1
<211> LENGTH: 28
<212> TYPE: PRT
<213> ORGANISM: Homo sapiens

<400> SEQUENCE: 1

Pro Gly Gly Phe Arg Gly Glu Phe Met Leu Gly Lys Pro Asp Pro Lys
1               5                   10                  15

Pro Glu Gly Lys Gly Leu Gly Ser Pro Tyr Ile Glu
            20                  25

<210> SEQ ID NO 2
<211> LENGTH: 65
<212> TYPE: PRT
<213> ORGANISM: Homo sapiens

<400> SEQUENCE: 2

Ser Ser Gln Pro Thr Ile Pro Ile Val Gly Ile Ile Ala Gly Leu Val
1               5                   10                  15

Leu Phe Gly Ala Val Ile Thr Gly Ala Val Val Ala Ala Val Met Trp
            20                  25                  30

Arg Arg Lys Ser Ser Asp Arg Lys Gly Gly Ser Tyr Ser Gln Ala Ala
        35                  40                  45

Ser Ser Asp Ser Ala Gln Gly Ser Asp Val Ser Leu Thr Ala Cys Lys
    50                  55                  60

Val
65

<210> SEQ ID NO 3
<211> LENGTH: 7
<212> TYPE: PRT
<213> ORGANISM: Homo sapiens

<400> SEQUENCE: 3

Lys Glu Glu Leu Trp Arg Gln
1               5

<210> SEQ ID NO 4
<211> LENGTH: 49
<212> TYPE: PRT
<213> ORGANISM: Homo sapiens

<400> SEQUENCE: 4
```

Asp Thr Ile Glu Val Pro Glu Lys Asp Leu Val Asp Lys Ala Arg Gln
1               5                   10                  15

Ile Asn Ile His Asn Leu Ser Ala Phe Tyr Asp Ser Glu Leu Phe Arg
            20                  25                  30

Met Asn Lys Phe Ser His Asp Leu Lys Arg Lys Met Ile Leu Gln Gln
            35                  40                  45

Phe

<210> SEQ ID NO 5
<211> LENGTH: 176
<212> TYPE: PRT
<213> ORGANISM: Homo sapiens

<400> SEQUENCE: 5

Arg Leu Leu Leu Ser Lys Gly His Ser Cys Tyr Arg Pro Arg Arg Thr
1               5                   10                  15

Gly Glu Arg Lys Arg Lys Ser Val Arg Gly Cys Ile Val Asp Ala Asn
            20                  25                  30

Leu Ser Val Leu Asn Leu Val Ile Val Lys Lys Gly Glu Lys Asp Ile
            35                  40                  45

Pro Gly Leu Thr Asp Thr Thr Val Pro Arg Arg Leu Gly Pro Lys Arg
    50                  55                  60

Ala Ser Arg Ile Arg Lys Leu Phe Asn Leu Ser Lys Glu Asp Asp Val
65                  70                  75                  80

Arg Gln Tyr Val Val Arg Lys Pro Leu Asn Lys Glu Gly Lys Lys Pro
            85                  90                  95

Arg Thr Lys Ala Pro Lys Ile Gln Arg Leu Val Thr Pro Arg Val Leu
            100                 105                 110

Gln His Lys Arg Arg Ile Ala Leu Lys Lys Gln Arg Thr Lys Lys
            115                 120                 125

Asn Lys Glu Glu Ala Ala Glu Tyr Ala Lys Leu Leu Ala Lys Arg Met
        130                 135                 140

Lys Glu Ala Lys Glu Lys Arg Gln Glu Gln Ile Ala Lys Arg Arg Arg
145                 150                 155                 160

Leu Ser Ser Leu Arg Ala Ser Thr Ser Lys Ser Glu Ser Gln Lys
                165                 170                 175

<210> SEQ ID NO 6
<211> LENGTH: 9
<212> TYPE: PRT
<213> ORGANISM: Homo sapiens

<400> SEQUENCE: 6

Glu Lys Arg Gln Glu Ile Thr Thr Glu
1               5

<210> SEQ ID NO 7
<211> LENGTH: 5
<212> TYPE: PRT
<213> ORGANISM: Homo sapiens

<400> SEQUENCE: 7

Ser Ile Ser Thr Ser
1               5

<210> SEQ ID NO 8
<211> LENGTH: 5
<212> TYPE: PRT
<213> ORGANISM: Homo sapiens

```
<400> SEQUENCE: 8

Ser Ser Gln Asp Val
1               5

<210> SEQ ID NO 9
<211> LENGTH: 23
<212> TYPE: PRT
<213> ORGANISM: Homo sapiens

<400> SEQUENCE: 9

Arg Ser Cys His His Gly Cys Thr Phe Thr Glu Asp Gln His Trp Glu
1               5                   10                  15

Cys Gly Glu Asp Asp Ala Val
            20

<210> SEQ ID NO 10
<211> LENGTH: 34
<212> TYPE: PRT
<213> ORGANISM: Homo sapiens

<400> SEQUENCE: 10

Ser Asn Ala Leu Glu Asn Phe Val Tyr Asn Lys Phe Gln Gln Asn Asn
1               5                   10                  15

Cys Val Trp Pro Gly Ala Val Ala His Ala Cys Asn Pro Ser Thr Leu
            20                  25                  30

Arg Gly

<210> SEQ ID NO 11
<211> LENGTH: 7
<212> TYPE: PRT
<213> ORGANISM: Homo sapiens

<400> SEQUENCE: 11

Gln Asp Ser Cys Gln Glu Asn
1               5

<210> SEQ ID NO 12
<211> LENGTH: 75
<212> TYPE: PRT
<213> ORGANISM: Homo sapiens

<400> SEQUENCE: 12

Ala Lys Arg Lys Glu Ala Gly Pro Leu Glu Val Val Thr Thr Pro
1               5                   10                  15

Ala Met Trp Arg Ser Leu Gly Leu Ala Leu Ala Leu Cys Leu Leu Pro
            20                  25                  30

Ser Gly Gly Thr Glu Ser Gln Asp Gln Ser Ser Leu Cys Lys Gln Pro
            35                  40                  45

Pro Ala Trp Ser Ile Arg Asp Gln Asp Pro Met Leu Asn Ser Asn Gly
        50                  55                  60

Ser Val Thr Val Val Ala Leu Leu Gln Ala Ser
65                  70                  75

<210> SEQ ID NO 13
<211> LENGTH: 23
<212> TYPE: PRT
<213> ORGANISM: Homo sapiens

<400> SEQUENCE: 13

Arg Gly Leu His Leu Pro Ser Gly Ala Pro Lys Asp Glu Pro Ser His
```

```
1               5              10              15
Ser Gly Met Glu Ser Thr Val
                20

<210> SEQ ID NO 14
<211> LENGTH: 32
<212> TYPE: PRT
<213> ORGANISM: Homo sapiens

<400> SEQUENCE: 14

Phe Ile Gly Arg Gly Asp Lys Pro Thr Glu Pro Gly Asp Ser Trp Leu
1               5                   10                  15

Ser Lys Ile Glu Ser Gln Phe Asn Phe Lys Phe Ala His Arg Thr Leu
                20                  25                  30

<210> SEQ ID NO 15
<211> LENGTH: 562
<212> TYPE: DNA
<213> ORGANISM: Homo sapiens

<400> SEQUENCE: 15
gcctggaggc ttcagaggtg aatttatgct tgggaagcct gatcccaaac ctgaagggaa    60
gggacttgga tctccttata ttgaataagc tgtttggagg aaggtgtctg tctgggagga   120
tggggcagta aatgaggttg gcagagtggc agtgggggct gcagagcc agccttggag    180 cctgctcatt ctgggccctt gctgccaagg agcccagcct cacctagcag gaaaggagat   240
gaaggccctc ctcccaggag gtagggtctt ggctgccccg aacttaaatg cttttgaaat   300
ctcttagatg tggaaatatt ttttcgaacc tgaaaatgca gctggtagaa tttcaatgga   360
agcataatcc atgtaaaata tattttagtt gatattttgt aaaatgcact ttttgtgtgt   420
gttgatcctg gtttcccaga tctgtatttc agtgtttaca agggaggaag gacctttcct   480
cacctccctt ttgacagaga ttagaagtac ttctttaaga aaaaaataaa tttgagaaat   540
tgtaaaaaaa aaaaaaaaaa aa                                            562

<210> SEQ ID NO 16
<211> LENGTH: 622
<212> TYPE: DNA
<213> ORGANISM: Homo sapiens

<400> SEQUENCE: 16
gtcttcccag cccaccatcc ccatcgtggg catcattgct ggcctggttc tctttggagc    60
tgtgatcact ggagctgtgg tcgctgctgt gatgtggagg aggaagagct cagatagaaa   120
aggagggagc tactctcagg ctgcaagcag tgacagtgcc cagggctctg atgtgtctct   180
cacagcttgt aaagtgtgag acagctgcct tgtgtgggac tgagaggcaa gagttgttcc   240
tgcccttccc tttgtgactt gaagaaccct gactttgttt ctgcaaaggc acctgcatgt   300
gtctgtgttc gtgtaggcat aatgtgagga ggtggggaga ccaccccacc cccatgtcca   360
ccatgaccct cttcccacgc tgacctgtgc tccctcccca atcatctttc ctgttccaga   420
gaggtggggc tgaggtgtct ccatctctgt ctcaacttca tggtgcactg agctgtaact   480
tcttccttcc ctattaaaat tagaacctga gtataaattt actttctcaa attcttgcca   540
tgagaggttg atgagttaat taaaggagaa gattcctaaa atttgagaga caaaataaat   600
ggaacacatg agaaaaaaaa aa                                            622

<210> SEQ ID NO 17
```

<211> LENGTH: 1172
<212> TYPE: DNA
<213> ORGANISM: Homo sapiens

<400> SEQUENCE: 17

```
aaggaagaac tatggcgaca gtaaaaagtg gttgccaaag aaagatcatg tcctttgcag      60
gaacatggat ggggctggag gccattatcc ttaacaaact aacataggaa caggaaacca     120
aatattccat gttctcacaa gtgggagtga ataacatgg acacaaagga ataacatact     180
ggggcctacc tgagggtgga gggtgggaaa agggacagga ccagaaaagt aactattggg     240
tactaggctt ccctacgtgc cgaattcggc acgtaggcct cgtgccgaat tcggcacgag     300
gctttattaa gggtggacta gtaataaaat ataatattct tgctgcttat gcagctgaca     360
ttgttgccct ccctaaagca accaagtagc ctttatttcc cacagtgaaa gaaacgctg     420
gcctatcagt tacattacaa aaggcagatt tcaagaggat tgagtaagta gttggatggc     480
tttcataaaa acaagaattc aagaagagga ttcatgcttt aagaaacatt tgttatacat     540
tcctcacaaa ttatacctgg gataaaaact atgtagcagg cagtgtgttt tccttccatg     600
tctctctgca ctacctgcag tgtgtcctct gaggctgcaa gtctgtccta tctgaattcc     660
cagcagaagc actaagaagc tccaacctat cacctagcag ataaacctat ggggaaaact     720
taaatctgtg catacatttc tggatgcatt tacttatctt taaaaaaaaa ggaatcctat     780
gacctgattt ggccacaaaa ataatcttgc tgtacaatc aatctcttgg aaattaagag     840
atcctatgga tttgatgact ggtattagag gtgacaatgt aaccgattaa caacagacag     900
caataacttc gttttagaaa cattcaagca atagctttat agcttcaaca tatggtacgt     960
tttaaccttg aaagttttgc aatgatgaaa gcagtatttg tacaaatgaa agcagaatt    1020
ctctttata tggtttatac tgttgatcag aaatgttgat tgtgcattga gtattaaaaa    1080
attagatgta tattattcat tgttcttttac tcatgagtac cttataataa taataatgta    1140
ttctttgtta acaaaaaaa aaaaaaaaaa aa                                   1172
```

<210> SEQ ID NO 18
<211> LENGTH: 826
<212> TYPE: DNA
<213> ORGANISM: Homo sapiens

<400> SEQUENCE: 18

```
ggacactatt gaggtccctg agaaggactt ggtggataag gctcgtcaga tcaacatcca      60
caacctctct gcattttatg acagtgagct cttcaggatg aacaagttca gccacgacct     120
gaaaaggaaa atgatcctgc agcagttctg aggccctatg ccatccataa ggattccttg     180
ggattctggt ttggggtggt cagtgccctc tgtgctttat ggacacaaaa ccagagcact     240
tgatgaactc ggggtactag ggtcagggct tatagcagga tgtctggctg cacctggcat     300
gactgtttgt ttctccaagc ctgctttgtg cttctcacct ttgggtggga tgccttgcca     360
gtgtgtctta cttggttgct gaacatcttg ccacctccga gtgctttgtc tccactcagt     420
accttggatc agagctgctg agttcaggat gcctgcgtgt ggtttaggtg ttagccttct     480
tacatggatg tcaggagagc tgctgccctc ttggcgtgag ttgcgtattc aggctgcttt     540
tgctgccttt ggccagagag ctggttgaag atgtttgtaa tcgttttcag tctcctgcag     600
gtttctgtgc cctgtggtg gaagagggca cgacagtgcc agcgcagcgt tctgggctcc     660
tcagtcgcag gggtgggatg tgagtcatgc ggattatcca ctcgccacag ttatcagctg     720
ccattgctcc ctgtctgttt ccccactctc ttatttgtgc attcggtttg gtttctgtag     780
```

-continued

```
ttttaatttt taataaagtt gaataaaata taaaaaaaaa aaaaaa              826
```

<210> SEQ ID NO 19
<211> LENGTH: 588
<212> TYPE: DNA
<213> ORGANISM: Homo sapiens

<400> SEQUENCE: 19

```
ccgcctgcta ctgagtaagg ggcattcctg ttacagacca aggagaactg gagaaagaaa    60
gagaaaatca gttcgtggtt gcattgtgga tgcaaatctg agcgttctca acttggttat   120
tgtaaaaaaa ggagagaagg atattcctgg actgactgat actacagtgc ctcgccgcct   180
gggcccccaaa agagctagca gaatccgcaa acttttcaat ctctctaaag aagatgatgt   240
ccgccagtat gttgtaagaa agcccttaaa taaagaaggt aagaaaccta ggaccaaagc   300
acccaagatt cagcgtcttg ttactccacg tgtcctgcag cacaaacggc ggcgtattgc   360
tctgaagaag cagcgtacca agaaaaataa agaagaggct gcagaatatg ctaaactttt   420
ggccaagaga atgaaggagg ctaaggagaa gcgccaggaa caaattgcga agagacgcag   480
actttcctct ctgcgagctt ctacttctaa gtctgaatcc agtcagaaat aagatttttt   540
gagtaacaaa taaataagat cagactctga aaaaaaaaa aaaaaaaa              588
```

<210> SEQ ID NO 20
<211> LENGTH: 409
<212> TYPE: DNA
<213> ORGANISM: Homo sapiens

<400> SEQUENCE: 20

```
gagaagaggc aagaaatcac tacagaatga aggaacatcc cttgaggtga cccagccaac    60
ctgtggccag aaggagggtt gtaccttgaa aagacactga aagcattttg gtgtgtgaag   120
taagggtggg cagaggaggt agaaaatcaa ttcaattgtc gcatcattca tggttctttta 180
atattgatgc tcagtgcatt ggccttagaa tatcccagcc tctcttctgg tttgctgagt   240
gctgtgtaag taagcatggt ggaattgttt ggggacatat atagtgatcc ttggtcactg   300
gtgtttcaac attctggaaa gtcacatcga tcaagaatat ttttattttt taagaaagca   360
taaccagcaa taaaaatact atttttgagt ctaaaaaaaa aaaaaaaaa              409
```

<210> SEQ ID NO 21
<211> LENGTH: 455
<212> TYPE: DNA
<213> ORGANISM: Homo sapiens

<400> SEQUENCE: 21

```
ctcgatctca acctcgtgat ccacccacct cggtctccca agcgctggga attacaggcg    60
tgagccaccg cgccaagcca aggtctgcat ttttctttag aactcagaac acccaatagt   120
cctaggcccc catcctcgca tggcagcaag ctaaataagc atcttccac tgcgagttgg    180
ggcatgaccc agcctatggt ttgccatact ccctcttttt ctccgttttt tcattaattg   240
tgaacctgac ctgcatcacc ctttcatgtc agtgctctcc aaacctgctt gcttgcaccc   300
ctctagtcga atattttgt gcttaccccca atatatgtgt gtgactattg aactctattc   360
gtagactgct tgtactaatg tcatttgcat cataaaatat tcatatccaa taaacatatt   420
aaaaggatga gataagaaaa aaaaaaaaaa aaaaa                             455
```

<210> SEQ ID NO 22

```
<211> LENGTH: 693
<212> TYPE: DNA
<213> ORGANISM: Homo sapiens

<400> SEQUENCE: 22
gagcagtcaa gatgtgtgac ttcaccgaag accagaccgc agagttcaag gaggccttcc      60
agctgtttga ccgaacaggt gatggcaaga tcctgtacag ccagtgtggg gatgtgatga     120
gggccctggg ccagaaccct accaacgccg aggtgctcaa ggtcctgggg aaccccaaga     180
gtgatgagat gaatgtgaag gtgctggact ttgagcactt tctgcccatg ctgcagacag     240
tggccaagaa caaggaccag ggcacctatg aggattatgt cgaaggactt cgggtgtttg     300
acaaggaagg aaatggcacc gtcatgggtg ctgaaatccg gcatgttctt gtcacactgg     360
gtgagaagat gacagaggaa gaagtagaga tgctggtggc agggcatgag acagcaatg      420 gttgtatcaa ctatgaagcg tttgtgaggc atatcctgtc ggggtgacgg gcccatgggg     480
cggagctcgt ccgcatggtg ctgaatggct gaggaccttc ccagtctccc cagagtccgt     540
gcctttccct gtgtgaattt tgtatctagc ctaaagtttc cctaggcttt cttgtctcag     600
caactttccc atcttgtctc tcttggatga tgtttgccgt cagcattcac caaataaact     660
tgctctctgg aaaaaaaaaa aaaaaaaaaa aaa                                  693

<210> SEQ ID NO 23
<211> LENGTH: 533
<212> TYPE: DNA
<213> ORGANISM: Homo sapiens

<400> SEQUENCE: 23
aagaagctgc caccatggtt gcactttcac tgaagatcag cattgggaat gtggtgaaga      60
cgatgcagtt tgagccgtct accatggtgt acgacgcctg ccgcatcatt cgtgagcgga     120
tcccagaggc cccagctggt cctcccagcg actttgggct cttt ctgtca gatgatgacc     180 ccaaaagggg tatatggctg gaggctggga agctttgga ctactacatg ctccgaaatg      240
gggacactat ggagtacagg aagaaacaga gacccctgaa gatccgtatg ctggatggaa     300
ctgtgaagac gatcatggtg gatgactcta gactgtcac tgacatgctc atgaccatct      360
gtgcccgcat tggcatcacc aatcatgatg aatattcatc agctctcttc accgtttttt     420
gatactatct tcccccaccc ccagctaccc ataggggctg cagagttata agccccaaac     480
aggtcatgct ccaataaaaa tgattctacc tacaaaaaaa aaaaaaaaaa aaa             533

<210> SEQ ID NO 24
<211> LENGTH: 1120
<212> TYPE: DNA
<213> ORGANISM: Homo sapiens

<400> SEQUENCE: 24
gtcaaatgct ctggagaact ttgtctataa caagtttcag tagaataact gtgtttggcc       60
gggcgccgtg gctcacgctt gtaatcccag cactttgaga gggtgaggcg ggaggatcac      120
ctgaggtagg agttcgagac cagcatagcc aacatgggga accccgtctc tactaaaaaa      180
tacaaaatta gccgggcgtg gtggcacgcg ctggtaatcc caactactcc agaggctgaa      240
gcaggagaat ccgttcaacc cgggaggtgg aggttgcggt gagccgaaat tgtgctgctg      300
cactgaagcc tggacaacaa agtgagacta cgtctcaaaa aaaaaaaaaa aaaaaaaagg      360
ccgggcgtgg tggctcacgc ctgtaatccc agcactttgg gaggccgagg cgggtggatc      420
acgaggtcag gagatcgaga ccatcctggc taacacggtg aaaccccgtc tctactgaaa      480
```

```
atacaaaaaa attagccggg cgtggtggcg ggcgcctata gtcccagcta cttgggaggc      540
tgaggcagga gaatggcgtg aacccgggag gcggagcttg cagtgagccg agatcgcgcc      600
actgcactcc agcctgggcg acagagcgag actccgtctc agaaaaaaaa aaaaaaaaaa      660
aggaataact gtgcttgaga atttaccatg ggataggata attaatattt ttccataaca      720
cataactaag attgactgta attttatta actttatttc tctagttgaa ttaatgataa       780
ttctccttta atgaagtatc gaaataaca actagttgcc aggtgggcgc ggtggctcac       840
acctgtaatc ccagcacttt gggaggccga ggtgggtgga tcacttgagg ccaggagttc      900
gagaccagcc tggccaaaat ggtgaaaccc cgtctctact aaaaaaaata caaacattag      960
ccaggcgtgg tgccaggcgc ctgtaatctc agctactcgg gaggctgtgg caggagaatc     1020
gctttagcct gggaggcgga ggttgcagtg agccgtgact gagccactgc actccagcct     1080
ggcaacagag tgagactgtg tctcaaaaaa aaaaaaaaa                            1120

<210> SEQ ID NO 25
<211> LENGTH: 291
<212> TYPE: DNA
<213> ORGANISM: Homo sapiens

<400> SEQUENCE: 25
caagattctt gccaagagaa ttaatgtgcg tattgagcac attaagcact ctaagagccg       60
agatagcttc ctgaaacgtg tgaaggaaaa tgatcagaaa aagaaagaag ccaaagagaa      120
aggtacctgg gttcaactaa agcgccagcc tgctccaccc agagaagcac actttgtgag      180
aaccaatggg aaggagcctg agctgctgga acctattccc tatgaattca tggcataata      240
ggtgttaaaa aaaaaaataa aggacctctg ggctacaaaa aaaaaaaaaa a              291

<210> SEQ ID NO 26
<211> LENGTH: 573
<212> TYPE: DNA
<213> ORGANISM: Homo sapiens

<400> SEQUENCE: 26
caaagagaaa ggaagcaggc ccgttggaag tggttgtgac aaccccagca atgtggagaa       60
gcctggggct tgccctggct ctctgtctcc tcccatcggg aggaacagag agccaggacc      120
aaagctcctt atgtaagcaa cccccagcct ggagcataag agatcaagat ccaatgctaa      180
actccaatgg ttcagtgact gtggttgctc ttcttcaagc cagctgatac ctgtgcatac      240
tgcaggcatc taaattagaa gacctgcgag taaaactgaa gaaagaagga tattctaata      300
tttcttatat tgttgttaat catcaaggaa tctcttctcg attaaaatac acacatctta      360
agaataaggt ttcagagcat attcctgttt atcaacaaga agaaaccaa acagatgtct       420 ggactctttt aaatggaagc aaagatgact tcctcatata tgatagatgt ggccgtcttg      480
tatatcatct tggtttgcct ttttccttcc taactttccc atatgtagaa gaagccatta      540
agattgctta ctgtgaaaaa aaaaaaaaaa aaa                                  573

<210> SEQ ID NO 27
<211> LENGTH: 544
<212> TYPE: DNA
<213> ORGANISM: Homo sapiens

<400> SEQUENCE: 27
gagaggttta cacctgccaa gtggagcacc caagcctgac gagccctctc acagtggaat       60
```

-continued

```
ggagagcacg gtctgaatct gcacagagca agatgctgag tggagtcggg ggcttcgtgc      120
tgggcctgct cttccttggg gccgggctgt tcatctactt caggaatcag aaaggacact      180
ctggacttca gccaacagga ttcctgagct gaagtgaaga tgaccacatt caaggaagaa      240
ccttctgccc cagctttgca ggatgaaaca cttccccgct tggctctcat tcttccacaa      300
gagagacctt tctccggacc tggttgctac tggttcagca gctctgcaga aaatgtcctc      360
ccttgtggct gcctcagctc gtacctttgg cctgaagtcc cagcattaat ggcagcccct      420
catcttccaa gttttgtgct cccctttacc taatgcttcc tgcctcccat gcatctgtac      480
tcctgctgtg ccacaaacac attacattat taaatgtttc tcaaacaaaa aaaaaaaaaa      540
aaaa                                                                  544
```

<210> SEQ ID NO 28
<211> LENGTH: 500
<212> TYPE: DNA
<213> ORGANISM: Homo sapiens

<400> SEQUENCE: 28

```
atttataggt agaggcgaca aacctaccga gcctggtgat agctggttgt ccaagataga       60
atcttagttc aactttaaat ttgcccacag aaccctctaa atccccttgt aaatttaact      120
gttagtccaa agaggaacag ctctttggac actaggaaaa aaccttgtag agagagtaaa      180
aaatttaaca cccatagtag gcctaaaagc agccaccaat taagaaagcg ttcaagctca      240
acacccacta cctaaaaaat cccaaacata taactgaact cctcacaccc aattggacca      300
atctatcacc ctatagaaga actaatgtta gtataagtaa catgaaaaca ttctcctccg      360
cataagcctg cgtcagatta aaacactgaa ctgacaatta acagcccaat atctacaatc      420
aaccaacaag tcattattac cctcactgtc aacccaacac aggcatgctc ataaggaaag      480
gttaaaaaaa aaaaaaaaaa                                                 500
```

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29

```
ttaccctctg actttgttca                                                  20
```

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30

```
cgccagggtt ttcccagtca cgac                                             24
```